US012161503B2

(12) United States Patent
Politis et al.

(10) Patent No.: US 12,161,503 B2
(45) Date of Patent: Dec. 10, 2024

(54) METHOD AND SYSTEM FOR MONITORING HEART FUNCTION BASED ON HEART SOUND CENTER OF MASS

(71) Applicant: Pacesetter, Inc., Sylmar, CA (US)

(72) Inventors: Nikolaos Politis, Berlin (DE); Jan O. Mangual-Soto, Rho (IT); Louis-Philippe Richer, Montreal (CA); Jong Gill, Valencia, CA (US); Fady Dawoud, Studio City, CA (US)

(73) Assignee: Pacesetter, Inc., Sylmar (CA)

( * ) Notice: Subject to any disclaimer, the term of this patent is extended or adjusted under 35 U.S.C. 154(b) by 411 days.

(21) Appl. No.: 17/667,146

(22) Filed: Feb. 8, 2022

(65) Prior Publication Data

US 2022/0361837 A1 Nov. 17, 2022

Related U.S. Application Data

(60) Provisional application No. 63/188,241, filed on May 13, 2021.

(51) Int. Cl.
*A61B 5/02* (2006.01)
*A61B 5/00* (2006.01)
(Continued)

(52) U.S. Cl.
CPC ............ *A61B 7/006* (2013.01); *A61B 5/0006* (2013.01); *A61B 5/0245* (2013.01); *A61B 5/29* (2021.01);
(Continued)

(58) Field of Classification Search
None
See application file for complete search history.

(56) References Cited

U.S. PATENT DOCUMENTS

2006/0155202 A1* 7/2006 Arand ...................... A61B 7/00
600/528
2019/0358464 A1* 11/2019 Volosin ................. A61B 5/024

FOREIGN PATENT DOCUMENTS

WO  2006076068  7/2006
WO  2017208040  12/2017

OTHER PUBLICATIONS

Ferdoushi et al., "A Spectral Centroid Based Analysis of Heart sounds for Disease Detection Using Machine Learning", 2019 IEEE International WIE Conference on Electrical and Computer Engineering (WIECON-ECE), IEEE, Nov. 15, 2019 ( 6 pages).

(Continued)

*Primary Examiner* — Ankit D Tejani
(74) *Attorney, Agent, or Firm* — Dean D. Small; The Small Patent Law Group, LLC

(57) ABSTRACT

A system and method for monitoring heart function based on heart sounds (HS) is provided. The system includes electrodes configured to sense electrical cardiac activity (CA) signals over a period of time. An HS sensor is configured to sense HS signals over the period of time. The system includes memory to store specific executable instructions and includes one or more processors that, when executing the specific executable instructions, is configured to: identify a characteristic of interest (COI) of a heartbeat from the CA signals. The processors overlay a HS search window onto an HS segment of the HS signals based on the COI from the CA signals and calculate a center of mass (COM) for at least one of S1 or S2 HS based on the HS segment of the HS signals within the search window to obtain a corresponding at least one of S1 COM or S2 COM. The processors calculate at least one of an electromechanical activation time (EMAT) or a systolic interval (SI) based on the at least one of S1 COM or S2 COM and record the at least one of the EMAT or SI.

20 Claims, 22 Drawing Sheets

(51) Int. Cl.
    *A61B 5/0245*    (2006.01)
    *A61B 5/29*      (2021.01)
    *A61B 5/352*     (2021.01)
    *A61B 7/00*      (2006.01)
(52) U.S. Cl.
    CPC .............. *A61B 5/352* (2021.01); *A61B 5/686* (2013.01); *A61B 2562/0219* (2013.01)

(56) References Cited

OTHER PUBLICATIONS

Erne Paul: "Review article Beyond auscultation—acoustic cardiography in the diagnosis and assessment of cardiac disease", Swiss Medical Weekly, vol. 138, No. 31-32, Aug. 9, 2008 (15 pages).
Extended European Search Report for related European Patent Application No. 22171242.5 dated Oct. 10, 2022 (10 pages).

* cited by examiner

METHOD AND SYSTEM FOR MONITORING HEART FUNCTION BASED ON HEART SOUND CENTER OF MASS

RELATED APPLICATIONS

The present application claims priority to U.S. Provisional Application Ser. No. 63/188,241, filed May 13, 2021, the complete subject matter of which is incorporated herein by reference in their entirety.

The present application relates to, and is filed on the same day as, co-pending U.S. application Ser. No. 17/667,172, filed Aug. 13, 2024, the complete subject matter of which is incorporated herein by reference in their entirety.

BACKGROUND

Embodiments of the present disclosure generally relate to methods and systems for monitoring heart function based on heart sounds.

Implantable medical devices (IMDs) are offered today for a wide variety of applications to monitor and treat various physiologic conditions. More recently, an interest has developed in utilizing heart sounds as a cardiac biomarker, such as in connection with providing clinically useful information related to ventricular contraction in various valve related diseases.

Miniaturized accelerometers have been proposed, that utilize micro-electromechanical system (MEMS) technology, to detect heart sounds while the accelerometers are implanted within an IMD. Conventional heart sound monitoring techniques generally monitor aspects such as the heart sound duration, heart sound amplitude, intervals between heart sound peaks, intervals between an R-wave peak and a heart sound peak and the like.

However, conventional approaches that utilize heart sounds may experience certain limitations. For example, various factors may affect the quality of the heart sound signals, such as the location and/or orientation of the IMD. When the quality of the heart sound signal is inferior, it becomes difficult to identify the heart sound characteristic of interest, such as the heart sound duration or peak. When the peak is incorrectly detected, the inaccuracy can lead to an incorrect determination of a corresponding interval, such as the interval between S1 and S2 peaks, the interval between the R-wave peak and the S1 peak, etc. Inaccuracies in the interval of interest can lead to incorrect determinations of heart function.

Further, some conventional approaches may analyze an "area under the curve" within the S1 and/or S2 heart sounds. However, calculations of the AOC for S1 and S2 heart sounds do not provide a particular time point within the heart sound for use in measuring intervals, such as between a point of interest in the QRS complex and a point in the S1 or S2 heart sound. Further, the AOC does support determination of the systolic interval as the AOC does not designate a specific point in each of the S1 and S2 heart sounds.

A need remains for improvements in monitoring heart function based on heart sounds.

SUMMARY

In accordance with embodiments herein, a system for monitoring heart function based on heart sounds (HS) is provided. The system includes electrodes configured to sense electrical cardiac activity (CA) signals over a period of time. An HS sensor is configured to sense HS signals over the period of time. The system includes memory to store specific executable instructions and includes one or more processors that, when executing the specific executable instructions, is configured to: identify a characteristic of interest (COI) of a heartbeat from the CA signals. The processors overlay a HS search window onto an HS segment of the HS signals based on the COI from the CA signals and calculate a center of mass (COM) for at least one of S1 or S2 HS based on the HS segment of the HS signals within the search window to obtain a corresponding at least one of S1 COM or S2 COM. The processors calculate at least one of an electromechanical activation time (EMAT) or a systolic interval (SI) based on the at least one of S1 COM or S2 COM and record the at least one of the EMAT or SI.

Optionally, the HS search window includes S1 and S2 search windows. The one or more processors may be configured to overlay the S1 and S2 search windows over corresponding HS segments. The one or more processors may be configured to align the S1 search window over the HS signals to begin at or near an R-wave peak. The R-wave peak may represent the COI. The one or more processors may be configured to align the S2 search window over the HS signals to begin a predetermined interval after one of an end of the S1 search window or an R-wave peak. The R-wave peak may represent the COI. The S1 COM and S2 COM may represent corresponding points in time along the CA and HS signals.

Optionally, the COI may occur at a COI point in time along the CA signals. The one or more processors may be configured to calculate the EMAT by subtracting the S1 COM from the COI point in time. The one or more processors may be configured to calculate the SI as a difference between the S1 COM and the S2 COM. The system may comprise an implantable medical device (IMD). The memory and the one or more processors may include an IMD memory and an IMD processor, respectively. The IMD processor may be configured to perform at least one of the identify, overlay or calculate operations.

Optionally, the system may include an external device (ED) configured to wireless communicate with the IMD. The memory and the one or more processors may include an ED memory and an ED processor, respectively. The ED processor may be configured to perform at least one of the identify, overlay and calculate operations. The ED may wirelessly receive the CA and HS signals. The ED processor may be configured to perform the identify, overlay and calculate operations. The HS sensor may include an accelerometer configured to collect multi-dimensional (MD) accelerometer data along at least two axes. The HS signals may correspond to the accelerometer data.

In accordance with embodiments herein, a computer implemented method for monitoring heart function based on heart sounds (HS) is provided. The method obtains electrical cardiac activity (CA) signals, sensed at implantable electrodes, over a period of time and obtains HS signals, sensed by an implantable HS sensor, over the period of time. The method is under control of one or more processors. The method identifies a characteristic of interest (COI) of a heartbeat from the CA signals and overlays a HS search window onto an HS segment of the HS signals based on the COI from the CA signals. The method calculates a center of mass (COM) for at least one of S1 or S2 HS based on the HS segment of the HS signals within the search window to obtain a corresponding at least one of S1 COM or S2 COM and calculates at least one of an electromechanical activation time (EMAT) or a systolic interval (SI) based on the at least one of S1 COM or S2 COM. The method records the at least one of the EMAT or SI.

Optionally, the HS search window may include S1 and S2 search windows. The one or more processors may be configured to overlay the S1 and S2 search windows over corresponding HS segments. The aligning operation may include aligning the S1 search window over the HS signals to begin at or near an R-wave peak. The R-wave peak may represent the COI. The aligning operation may further comprise aligning the S2 search window over the HS signals to begin a predetermined interval after one of an end of the S1 search window or an R-wave peak. The R-wave peak may represent the COI.

Optionally, the calculating the S1 COM may comprise calculating products of i) amplitudes of the HS signals at points along the S1 search window and ii) positions of the corresponding points along the S1 search window; summing the products to form a first sum; summing the amplitudes of the HS signals at the points to form a second sum; and dividing the first sum by the second sum.

Optionally, the COI may occur at a COI point in time along the CA signals. The method may calculate the EMAT by subtracting the S1 COM from the COI point in time. The method may store the EMAT and SI over a period of time and monitoring an EMAT trend and an SI trend over a period of time for an indication of a change in a physiologic or non-physiologic condition. The method may wirelessly transmit the CA and HS signals from an implantable medical device (IMD) to an external device (ED). The ED may perform at least one of the identifying, overlaying, calculating and recording operations. The identify, overlay or calculate operations may be implemented by an implantable medical device.

In accordance with embodiments herein, a leadless IMD is provided that comprises: a housing; a fixation element coupled to the housing and configured to secure the IMD in or proximate to a local chamber of the heart; electrodes provided on the housing and configured to sense electrical cardiac activity (CA) signals over a period of time; an HS sensor configured to sense HS signals over the period of time; memory to store specific executable instructions; and one or more processors that, when executing the specific executable instructions, is configured to: identify a characteristic of interest (COI) of a heartbeat from the CA signals; calculate a center of mass (COM) for at least one HS based on the HS signals to obtain a corresponding at least one HS COM; and calculate at least one of a therapy-related (TR) delay or a sensing-related (SR) blanking interval (BI) based on the at least one HS COM.

Optionally, the identify and calculate operations are performed in a calibration mode. The calculate operations comprise: calculating an S1 COM and an S2 COM; calculating a diastolic interval (DI) based on the S1 COM and the S2 COM; and calculating an AV delay by subtracting a delta value from the DI. Optionally, the one or more processors is further configured, when in a therapy mode, to collect and analyze HS signals to identify an HS of interest on a beat by beat basis. Optionally, the one or more processors is further configured, when in the therapy mode, to manage delivering of therapy based on the HS of interest and the at least one of the TR delay or SR BI. Optionally, the one or more processors is further configured, in response to identifying the HS of interest, to start one or more event timers corresponding to the at least one of the TR delay or SR BI. Optionally, the IMD is configured to be implanted in or proximate to a ventricle, the at least one TR delay including an AV delay calculated by subtracting a delta value from a diastolic interval defined as the interval between an S1 COM and an S2 COM, the one or more processors is further configured to: identify an S2 HS; in response to the identifying the S2 HS, start an AV timer corresponding to the AV delay; and deliver a ventricular therapy when an intrinsic ventricular event is not detected before the AV timer times out.

Optionally, the at least one of the TR delay or SR BI is calculated by combining a delta value and at least one of a systolic interval, diastolic interval, S1-S1 interval, S2-S2 interval, S3-S3 interval, S4-S4 interval. S1-R-wave interval, S2-R-wave interval, S3-R-wave interval, or S4-R-wave interval. Optionally, the IMD further comprises a sensor configured to obtain heart rate (HR) data, the one or more processors configured to store the HR data with the at least one of TR delay or the SR BI to associate a first HR with at least one of a first TR delay or first SR BI and to associate a second HR with at least one of a second TR delay or second SR BI.

In accordance with embodiments herein, a computer implemented method for monitoring heart function based on heart sounds (HS) in a leadless implantable medical device (IMD), the method comprising: obtaining electrical cardiac activity (CA) signals, sensed at implantable electrodes provided on the leadless IMD, over a period of time; obtaining HS signals, sensed by an implantable HS sensor, over the period of time; under control of one or more processors, identifying a characteristic of interest (COI) of a heartbeat from the CA signals; calculating a center of mass (COM) for at least one HS based on the HS signals to obtain a corresponding at least one HS COM; and calculating at least one of a therapy-related (TR) delay or a sensing-related (SR) blanking interval (BI) based on the at least one HS COM.

Optionally, the identifying and calculating operations are performed in a calibration mode, and wherein, the calculating operations comprise: calculate an S1 COM and an S2 COM; calculate a diastolic interval (DI) based on the S1 COM and the S2 COM; and calculate an AV delay by subtracting a delta value from the DI. Optionally, the method further comprises, when in a therapy mode, collecting and analyzing HS signals to identify an HS of interest on a beat by beat basis. Optionally, the method further comprises, when in the therapy mode, managing delivering of therapy based on the HS of interest and the at least one of the TR delay or SR BI. Optionally, the method further comprises, in response to identifying the HS of interest, starting one or more event timers corresponding to the at least one of the TR delay or SR BI. Optionally, the IMD is configured to be implanted in or proximate to a ventricle, the at least one TR delay including an AV delay calculated by subtracting a delta value from a diastolic interval defined as the interval between an S1 COM and an S2 COM, the method further comprising: identifying an S2 HS; in response to the identifying the S2 HS, starting an AV timer corresponding to the AV delay; and delivering a ventricular therapy when an intrinsic ventricular event is not detected before the AV timer times out. Optionally, the at least one of the TR delay or SR BI is calculated by combining a delta value and at least one of a systolic interval, diastolic interval, S1-S1 interval, S2-S2 interval, S3-S3 interval, S4-S4 interval. S1-R-wave interval, S2-R-wave interval, S3-R-wave interval, or S4-R-wave interval.

In accordance with embodiments herein, a leadless implantable medical device (IMD) is provided that comprises: a housing; a fixation element coupled to the housing and configured to secure the IMD in or proximate to a local chamber of the heart; electrodes provided on the housing and configured to sense electrical cardiac activity (CA) signals over a period of time; an HS sensor configured to sense HS signals over the period of time; memory to store specific executable instructions and to store at least one of a therapy-related (TR) delay or a sensing-related (SR) blanking interval (BI), the at least one of the TR delay or SR BI based on at least one HS center of mass (COM) determined based on the HS signals; and one or more processors that, when executing the specific executable instructions, is configured, when in a therapy mode, to: collect and analyze HS signals to identify an HS of interest on a beat by beat basis; and manage delivery of therapy based on the HS of interest and the at least one of the TR delay or SR BI.

Optionally, the one or more processors are further configured, in response to identifying the HS of interest, to start one or more event timers corresponding to the at least one of the TR delay or SR BI. Optionally, the IMD is configured to be implanted in or proximate to a ventricle, the at least one TR delay including an AV delay calculated by subtracting a delta value from a diastolic interval defined as the interval between an S1 COM and an S2 COM, the one or more processors further configured to: identify an S2 HS; in response to the identifying the S2 HS, start an AV timer corresponding to the AV delay; and deliver a ventricular therapy when an intrinsic ventricular event is not detected before the AV timer times out. Optionally, the IMD is configured to be implanted in or proximate to a ventricle, the at least one TR delay including at least one of an HS-HS interval or an HS-R-wave interval calculated by combining a delta value with a corresponding at least one of the HS-HS interval or the HS-R-wave interval, the one or more processors further configured to: identify an HS of interest; in response to the identifying the HS of interest, start a timer corresponding to the at least one of the HS-HS interval or HS-R-wave interval; and deliver a ventricular therapy when an intrinsic ventricular event is not detected before the timer times out. Optionally, the IMD further comprises a sensor configured to obtain heart rate (HR) data, the one or more processors configured to adjust the at least one of the TR delay or SR BI based on the HR data.

DETAILED DESCRIPTION

Figure 1A:
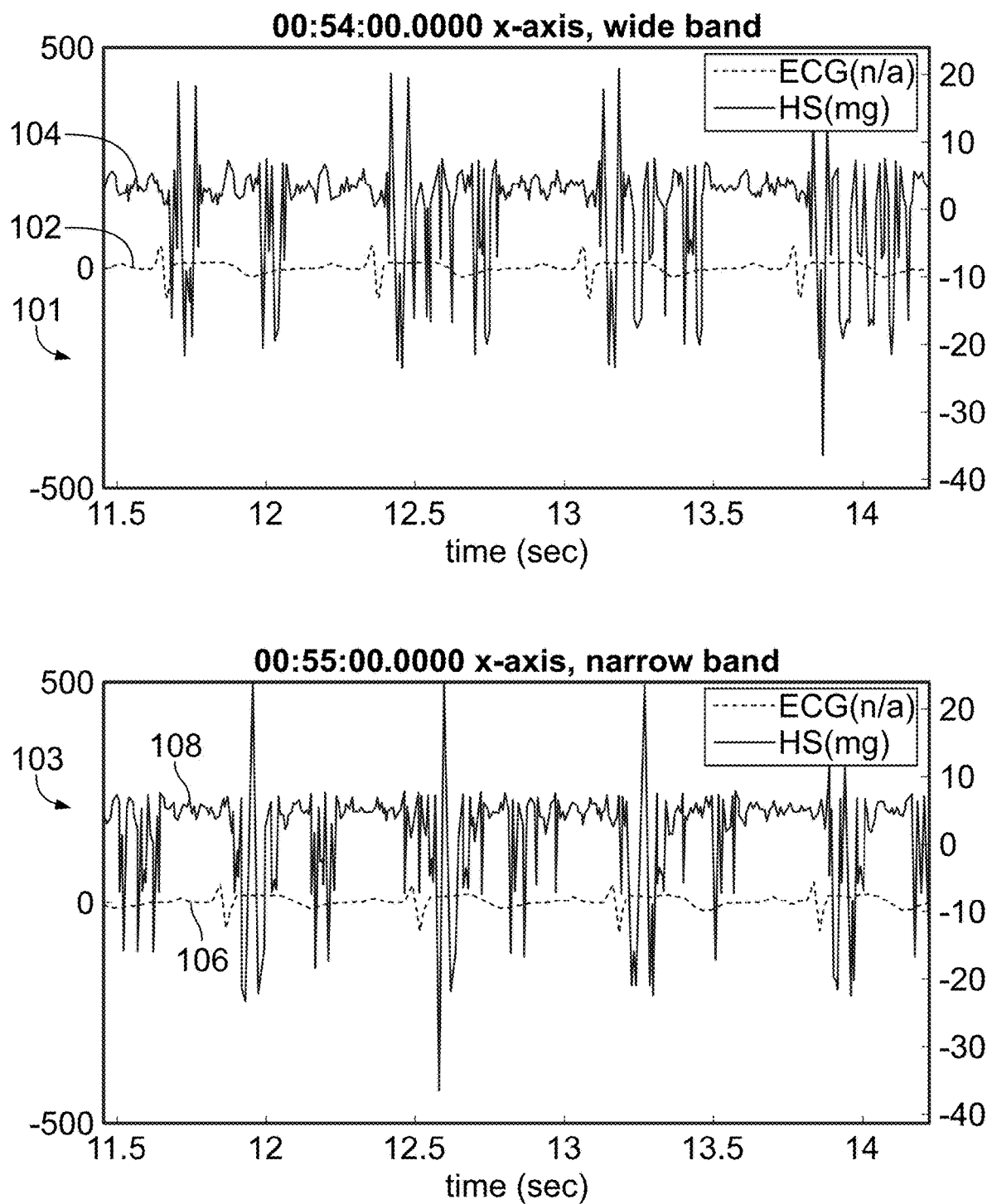
FIG. 1A illustrates examples of simultaneously recorded CA signals and corresponding HS signals to be processed in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein. For example, an IMD includes IMD memory and one or more IMD processors, while each external device/system (ED) (e.g., local, remote or anywhere within the healthcare system) include ED memory and one or more ED processors.

Terms

The terms "aggregate" and "composite" are used interchangeably to refer to a mathematical combination of two or more data values, signals and the like (e.g., mean, sum, average, median, normalization, etc.).

The terms "posture" and "patient posture" refer to postural states and/or activity levels of a patient including supine, laying on a right side, laying on a left side, sitting, standing, isometric arm exercises (e.g., pushing, pulling, and the like), ballottement, chest thump, device pressure (e.g., top, mid, and base), arm flap, handshake, and the like.

The term "activity level" refers to intensity and/or types of activity currently experienced by a patient at a point in time, including stationary state, rest state, exercise state, walking state, and the like.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes and/or by electrodes positioned within or proximate to the heart wall and/or chambers of the heart.

The terms "health care system" and "digital health care system" are used interchangeably throughout to reference to a system that includes equipment for measuring health parameters, and communication pathways from the equipment to secondary devices. The secondary devices may be at the same location as the equipment, or remote from the equipment at a different location. The communication pathways may be wired, wireless, over the air, cellular, in the cloud, etc. In one example, the healthcare system provided may be one of the systems described in U.S. Provisional Pat. App. No. 62/875,870 entitled METHODS DEVICE AND SYSTEMS FOR HOLISTIC INTEGRATED HEALTHCARE PATIENT MANAGEMENT, to Rupinder, filed Jul. 18, 2019, the entire contents of which are incorporated in full herein. Other patents that describe example monitoring systems include U.S. Pat. No. 6,572,557; entitled SYSTEM AND METHOD FOR MONITORING PROGRESSION OF CARDIAC DISEASE STATE USING PHYSIOLOGIC SENSORS, filed Dec. 21, 2000, to Tchou et al.; U.S. Pat. No. 6,480,733 entitled METHOD FORMONITORING HEART FAILURE filed Dec. 17, 1999, to Turcott; U.S. Pat. No. 7,272,443 entitled SYSTEM AND METHOD FOR PREDICTING A HEART CONDITION BASED ON IMPEDANCE VALUES USING AN IMPLANTABLE MEDICAL DEVICE, filed Dec. 14, 2004, to Min et al; U.S. Pat. No. 7,308,309 entitled DIAGNOSING CARDIAC HEALTH UTILIZING PARAMETER TREND ANALYSIS, filed Jan. 11, 2005, to Koh; and U.S. Pat. No. 6,645,153 entitled SYSTEM AND METHOD FOR EVALUATING RISK OF MORTALITY DUE TO CONGESTIVE HEART FAILURE USING PHYSIOLOGIC SENSORS, filed Feb. 7, 2002, to Kroll et. al., the entire contents of which are incorporated in full herein.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The terms "artificial intelligence", "machine learning" and "self-learning" are used interchangeably throughout and shall mean an artificial intelligence algorithm that learns from various automatic or manual inputs, such as features of interest, prior device classified arrhythmias, observations and/or data. The machine learning algorithm is adjusted over multiple iterations based on the features of interest, posture, HS signals, S1 COM, S2 COM, EMAT, SI, CA signals, characteristics of interest of the CA signals, prior device classified arrhythmias, observations and/or data. For example, the machine learning algorithm is adjusted by supervised learning, unsupervised learning, and/or reinforcement learning. Non-limiting examples of machine learning algorithms are a convolutional neural network, gradient boosting random forest, decision tree, K-means, deep learning, artificial neural network, and/or the like.

The term "subcutaneous" shall mean below the skin, but not intravenous. For example, a subcutaneous electrode/lead does not include an electrode/lead located in a chamber of the heart, in a vein on the heart, or in the lateral or posterior branches of the coronary sinus.

The terms "RA", "LA", "RV", and "LV" shall mean the right atrium, left atrium, right ventricle and left ventricle, respectively.

The term "leadless" generally refers to an absence of electrically-conductive leads that traverse vessels or other anatomy outside of the intra-cardiac space, while "intra-cardiac" means generally, entirely within the heart and associated vessels, such as the superior vena cava (SVC), inferior vena cava (IVC), coronary sinus (CS), coronary veins (CV), pulmonary arteries, and the like.

The term "COI" refers to a characteristic of interest within CA signals. Non-limiting examples of COI from a PQRST complex, include an R-wave, P-wave, T-wave and isoelectric segments. Non-limiting examples of COI from CA signals collected at an individual electrode(s) include a sensed event (e.g., an intrinsic event or evoked response). The COI may correspond to a peak of an individual sensed event, R-wave, an average or median P, R or T-wave peak and the like.

The term "notification" shall mean a communication and/or device command to be conveyed to one or more individuals and/or one or more other electronic devices, including but not limited to, network servers, workstations, laptop computers, tablet devices, smart phones, IMDs, equipment and the like.

Overview

In accordance with new and unique aspects herein, methods and devices are described that incorporate an accelerometer into an implantable medical device, such as an implantable cardiac monitor (ICM), to simultaneously record heart sounds (HS) and cardiac activity (CA) signals. The methods and devices identify a center of mass (COM) for HS S1 and S2 and utilize the S1 COM and S2 COM to monitor heart function, such as by recording electromechanical activation time (EMAT), systolic interval (SI), diastolic interval (DI), S1-S1 interval, S2-S2 interval, S3-S3 interval, S4-S4 interval and the like. The EMAT is representative of how electrical conduction translates to mechanical activity. The EMAT may be tracked by recording a time period between an occurrence of a QRS complex (e.g., the peak of the Q-wave) in the CA signals and the S1 COM. Additionally or alternatively, the SI may be tracked by recording a time period between the S1 COM and the S2 COM.

In accordance with new and unique aspects herein, the accelerometer may represent a three-dimensional accelerometer configured to detect heart sounds along three orthogonal axes (e.g., an X-axis, Y-axis and Z-axis) with respect to a device reference axis. Applicants have recognized that, due to the vibratory nature of HS signals measured by an accelerometer, there may be a challenge in detecting consistent timing of the S1 and S2 signals. To address this challenge, embodiments herein calculate the center of mass associated with each S1 heart sound and each S2 heart sound. Applicant has further recognized that an additional challenge exists in determining when a heart sound begins and ends, and more generally where the heart sound is located along a temporal timeline. To address this challenge, embodiments herein utilize a characteristic of interest from the PQRST complex, such as the peak of the R-wave, peak of the Q-wave and the like to define and temporally locate heart sound search windows for the S1 and S2 heart sounds.

Additionally or alternatively, to further improve the accuracy of monitoring the S1 and S2 heart sounds, filter parameters are customized for filters that process the accelerometer signals along each of the X, Y and Z axes.

Figure 1B:
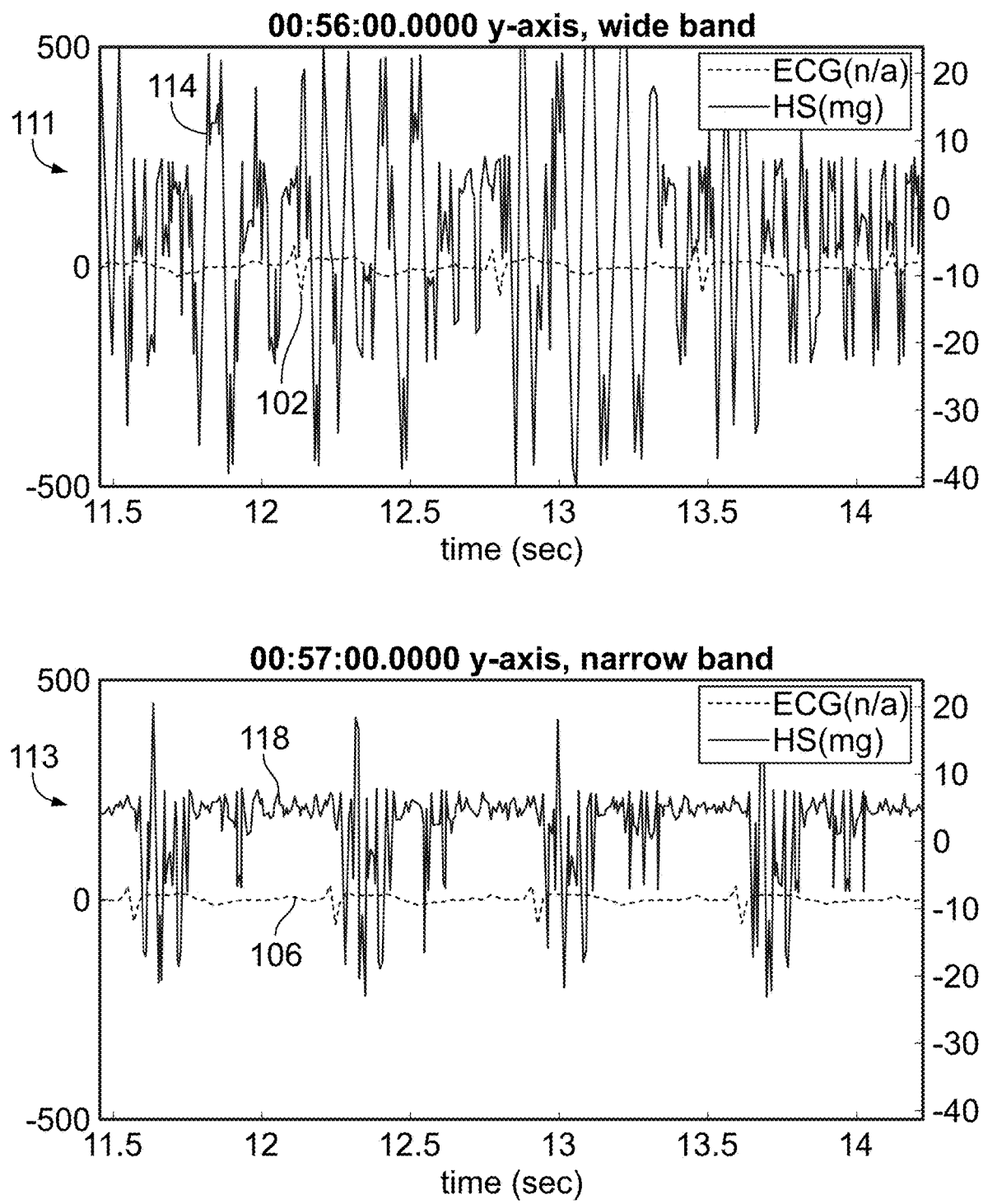
FIG. 1B illustrates examples of simultaneously recorded CA signals and corresponding HS signals to be processed in accordance with embodiments herein.
Figure 1C:
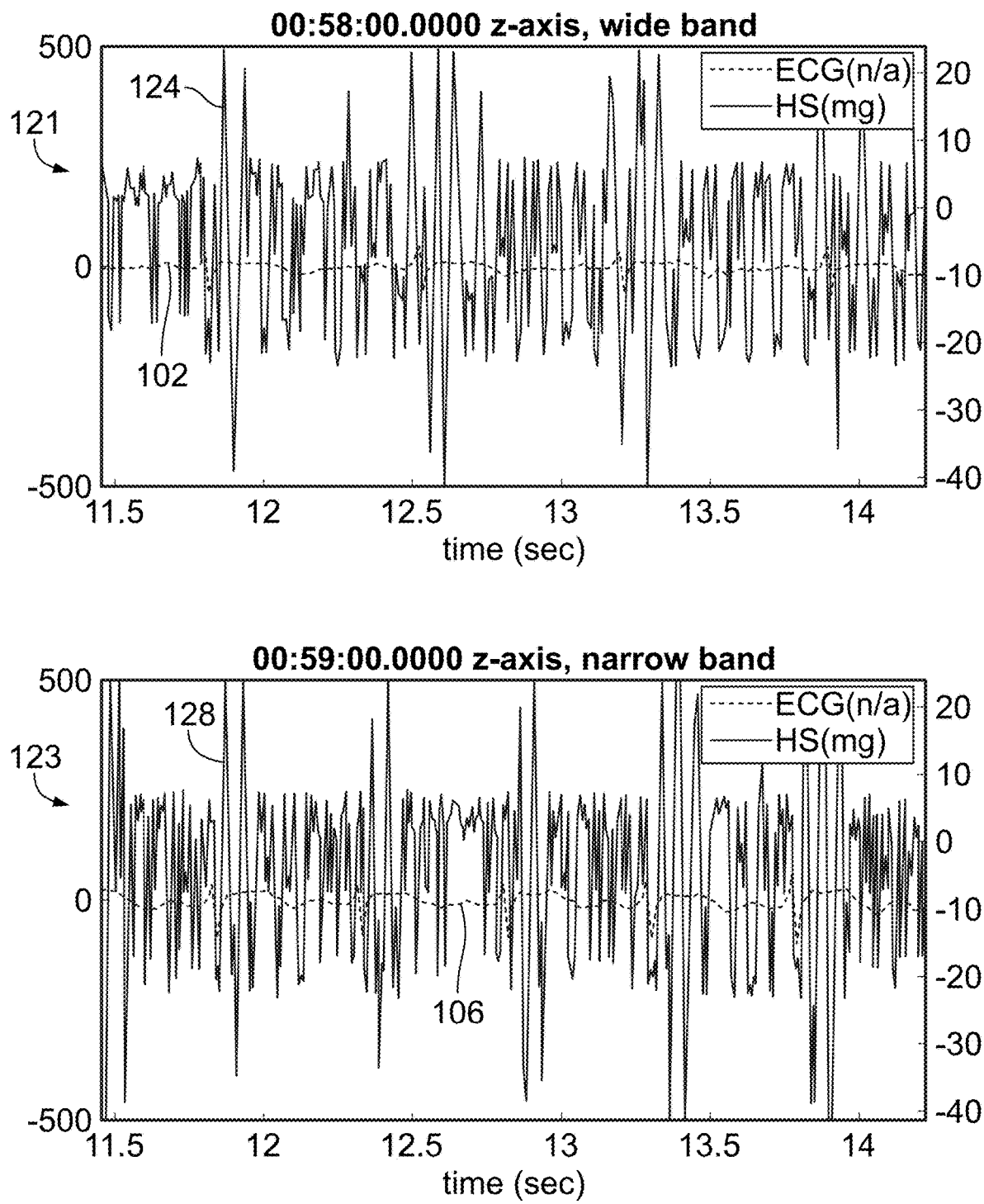
FIG. 1C illustrates examples of simultaneously recorded CA signals and corresponding HS signals to be processed in accordance with embodiments herein.

FIGS. 1A-1C illustrate examples of simultaneously recorded CA signals and corresponding HS signals to be processed in accordance with embodiments herein. In FIG. 1A, the upper and lower panels 101, 103 illustrate an electrogram (EGM) signal, as a CA signal 102, 106 recorded over slightly more than three seconds. The upper and lower panels 101, 103 further illustrate heart sound signals 104, 108 recorded at the same time over the same period of time. The heart sound signals 104, 108 are collected along a first axis (e.g., an x-axis) of the accelerometer. The heart sound signals 104 collected in the upper panel 101 represent a signal that has been processed utilizing a wideband filter, while the heart sound signals 108 in the lower panel 103 represent a signal that has been processed utilizing a narrowband filter. By way of example, the wideband filter may have a passband of between 7.5 Hz and 100 Hz, while the narrowband filter may have a passband between 15 Hz and 100 Hz.

In FIG. 1B, the upper and lower panels 111, 113 illustrate the same CA signal 102, 106. The upper and lower panels 111, 113 further illustrate heart sound signals 114, 118 recorded at the same time over the same period of time but utilizing different wideband and narrowband filters. However, the heart sound signals 114, 118 are collected along a different second axis (e.g., a Y-axis) of the accelerometer. The passbands for the wideband and narrowband filters utilized with the Y-axis may be the same or differ from the passbands utilized for the X-axis and/or Z-axis.

In FIG. 1C, the upper and lower panels 121, 123 illustrate the same CA signal 102, 106. The upper and lower panels 121, 123 further illustrate heart sound signals 124, 128 recorded at the same time over the same period of time but utilizing different wideband and narrowband filters. However, the heart sound signals 124, 128 are collected along a different third axis (e.g., a z-axis) of the accelerometer. The passbands for the wideband and narrowband filters utilized with the Z-axis may be the same or differ from the passbands utilized for the X-axis and/or Y-axis.

A visual comparison of the heart sound signals illustrated in FIGS. 1A-1C, shows that the heart sound signals will greatly differ depending upon the axis of the accelerometer utilized for collection and the filter. The filter parameters may be adjusted prior to implant, at the time of implant or at a later time during a clinical visit to achieve a desired builder output. Additionally or alternatively, one or more axes of the accelerometer may be chosen to sense HS signals based on various criteria.

Figure 2:
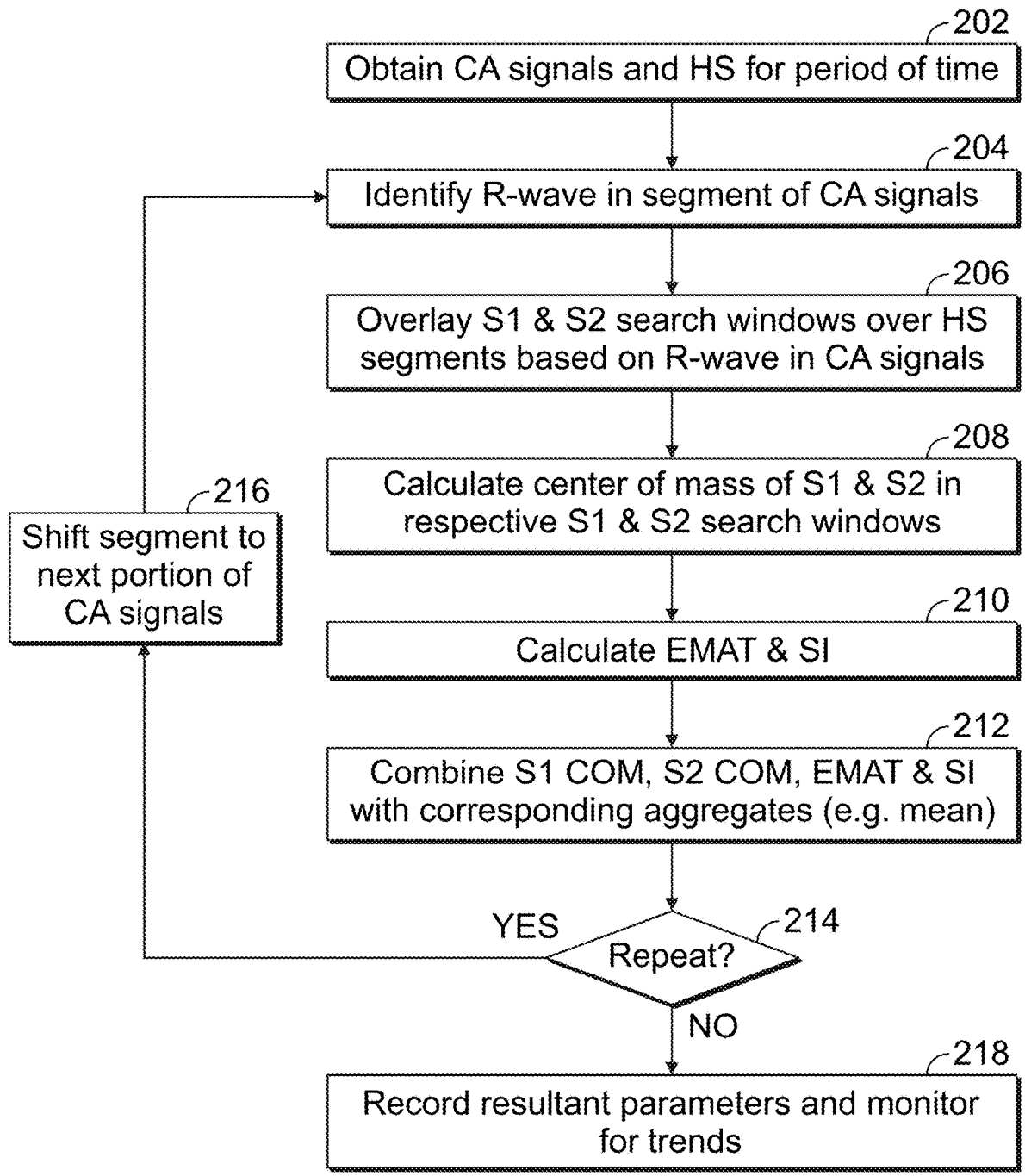
FIG. 2 illustrates a method for monitoring heart function based on heart sounds in accordance with embodiments herein.

FIG. 2 illustrates a method for monitoring heart function based on heart sounds in accordance with embodiments herein. The operations of FIG. 2 may be implemented by hardware, firmware, circuitry and/or one or more processors housed partially an/or entirely within an IMD, a local external device, remote server or more generally within a healthcare system. Optionally, the operations of FIG. 2 may be partially implemented by an IMD and partially implemented by a local external device, remote server or more generally within a healthcare system. For example, the IMD includes IMD memory and one or more IMD processors, while each of the external devices/systems (ED) (e.g., local, remote or anywhere within the healthcare system) include ED memory and one or more ED processors.

At 202, one or more processors obtain CA signals and HS signals for a common period of time. For example, the period of time may represent a predetermined number of seconds, minutes or otherwise, or alternatively a number of cardiac beats. The CA signals may be sensed utilizing one or more combinations of electrodes and sensing circuitry within coupled to the IMD. The HS signals may be sensed utilizing a three-dimensional accelerometer and HS filtering circuitry within the IMD.

At 204, the one or more processors identify a COI within a segment of the CA signals. For example, the segment may have a duration approximating the duration of a single heartbeat and the COI may represent the peak of the Q-wave, peak of the R-wave or otherwise.

At 206, the one or more processors overlay S1 and S2 search windows onto respective HS segments of the HS signals where the positions of the S1 and S2 search windows are determined based on the COI from the CA signal segment. For example, when the COI represents the peak of the R-wave, the S1 search window may be positioned to begin at the same time as the R-wave peak or a predetermined first interval before or after the R-wave peak. The S2 search window may then be positioned to begin a predetermined second interval after the R-wave peak and/or a predetermined third interval after the end of the S1 search window. The S1 and S2 search windows each have a corresponding duration that is sufficient to span from prior to a beginning and extend past an ending of the corresponding S1 and S2 heart sounds. For example, the S1 and S2 search windows may be preprogrammed to be 250 ms each.

At 208, the one or more processors calculate a center of mass for the S1 HS and a center of mass for the S2 HS to obtain an S1 COM and an S2 COM. The S1 COM represents a center of mass for the S1 signals within the corresponding S1 search window. The S2 COM represents a center of mass for the S2 signals within the corresponding S2 search window. For example, the COM may be calculated according to the following equation 1:

$$COM = \frac{\sum_{n=1}^{250} HSAmp * n}{\sum_{n=1}^{250} HSAmp} \qquad \text{Equation 1}$$

The variable HS Amp corresponds to the amplitude of the heart sound at the corresponding point "n" along the search window, while "n" corresponds to the point in time (e.g., in milliseconds). In the present example, the search window has a length corresponding to 250 data points. Stated another way, the COM is calculated by calculating products of i) the HS amplitude at each point along the search window and ii) the position of each corresponding point along the S1 or S2 search window (e.g., "n" equals 1-250). The products are then summed and divided by the sum of the individual HS amplitudes. More specifically, the one or more processors sum the products to form a first sum, sum the amplitudes of the HS signals at the points to form a second sum; and divide the first sum by the second sum. Equation 1 is repeated for the S1 search window and the S2 search window to obtain the S1 COM and the S2 COM. The resulting S1 COM and S2 COM represent first and second points in time, respectively, along a timeline corresponding to the CA signals and HS signals. The S1 COM is also referred to a S1 COM timing or S1_COM point in time. The S2 COM is also referred to a S2 COM timing or S2_COM point in time, At 210, the one or more processors calculate various indicators of heart function, such as an EMAT and an SI. The EMAT may be calculated as an interval between the peak of the R-wave and the S1 COM. For example, the EM 18 may be calculated to use Equation 2 (below):

$$\text{EMAT=S1\_COM-R\_wave\_loc,} \qquad \text{Equation 2}$$

The variable S1_COM represents the point in time for the center of mass for the S1 HS, while the variable R_wave_loc represents the point in time for the peak of the R-wave. Additionally or alternatively, the S1_COM and R_wave_loc variables may be combined in other mathematical combinations that are also indicative of the EMAT.

As another example, the SI may be calculated as an interval between the S1_COM and the S2_COM within a single heartbeat or cardiac cycle, such as using Equation 3 (below):

$$\text{SI=S2\_COM-S1\_COM} \qquad \text{Equation 3}$$

The variable S2_COM represents the point in time for the center of mass of the S2 HS in a current heartbeat or cardiac cycle and the variable S1_COM represents the point in time for the center of mass of the S1 HS in the same heartbeat or cardiac cycle. Additionally or alternatively, the S1_COM and S2_COM variables may be combined in other mathematical combinations that are also indicative of the SI. Additionally or alternatively, other intervals and times may be calculated, that are indicative of heart function, based on the S1 COM and/or S2 COM, and additional characteristics from the CA signals. Additionally or alternatively, the diastolic interval (DI) may be calculated as an interval between the S2_COM and the S1_COM within a single heartbeat or cardiac cycle, such as using Equation 4 (below):

$$\text{DI=S1\_COM-S2\_COM} \qquad \text{Equation 4.}$$

At 212, the one or more processors combine a most recently calculated S1 COM with an aggregate set of previously calculated S1 COMs. The one or more processors also combine the most recently calculated S2 COM with an aggregate set of previously calculated S2 COMs. The one or more processors also combine the most recently calculated EMAT and SI with an aggregate set of previously calculated EMATs and SIs, respectively.

At 214, the one or more processors determine whether to repeat the operations at 204-212. The operations at 204-212 are repeated for the CA signals and HS signals obtained for a select period of time. For example, if the period to time corresponds to one minute, while each iteration through the operations at 204-212, the one or more processors analyze a one second segment, the operations at 204-212 will be repeated 60 or more times. Based on the decision at 214, flow branches to 216 or to 218.

At 216, the one or more processors shift the segment to be analyzed to a next portion of the HS and CA signals. For example, when the CA signal segment that is analyzed is one second in length, the segment may be shifted a full one second forward in time such that the next segment does not overlap the prior segment. Alternatively, the segment may be shifted a percentage of the length of the segment (e.g., 25%), such that the next segment partially overlaps the prior segment. Thereafter, the operations at 204-212 are repeated for the next segment of the CA signals. The next R-wave is detected, which then defines the positions for the next S1 and S2 search windows. New S1 COM and S2 COM are calculated for the heart sounds within the new S1 and S2 search windows. New EMAT and SI are calculated based on the new R-wave, S1 COM and S2 COM. The new values are then combined with the aggregates, such as maintaining an average or mean over the results from each iteration through 204-212.

At 214, when the process determines that the entire CA signals and HS signals have been analyzed, flow moves to 218 where the one or more processors store the resultant parameter values. In addition, at 218, the one or more processors compare the stored resultant parameter values to previously stored resultant parameter values to monitor trends.

Figure 3:
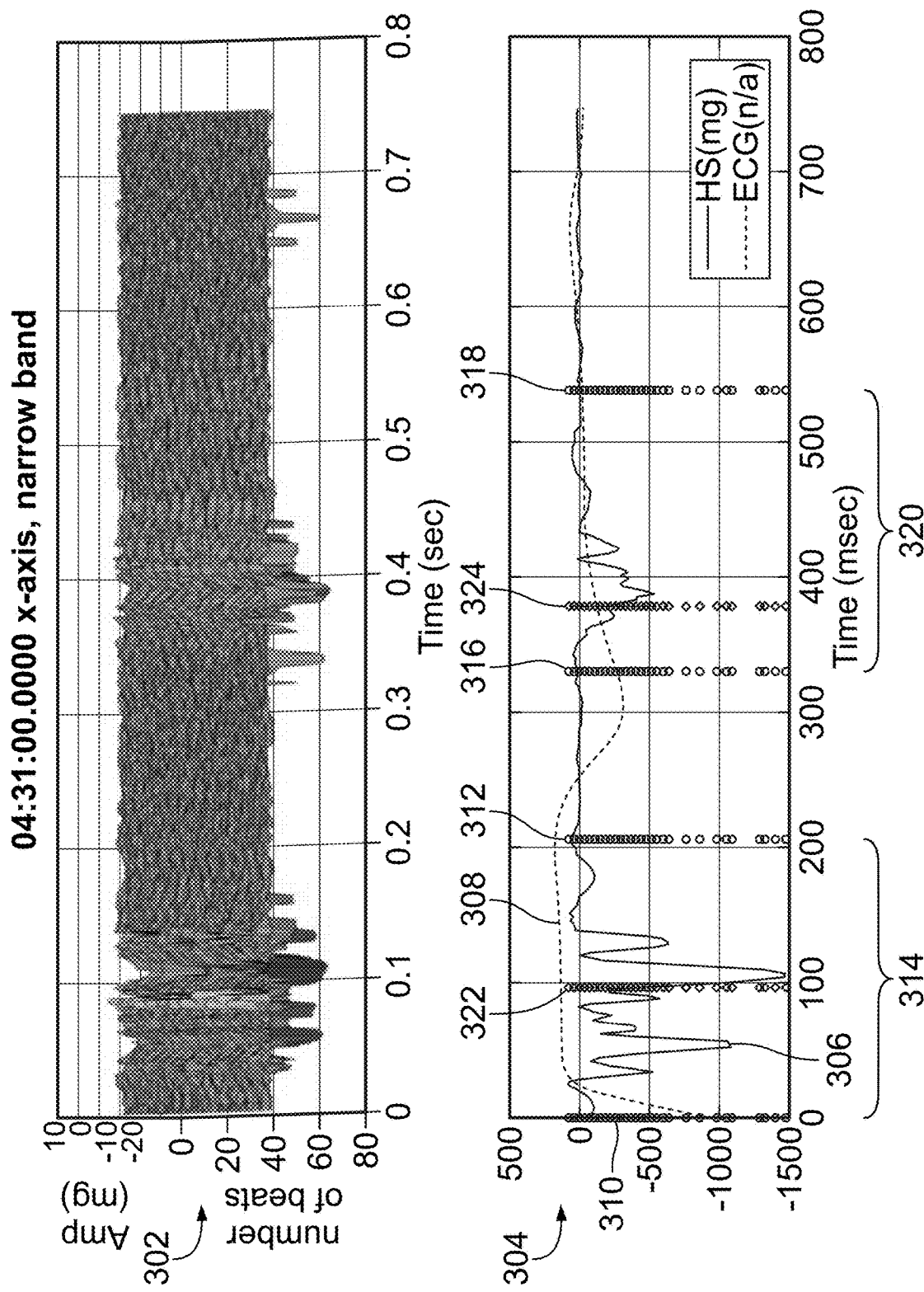
FIG. 3 illustrates a graphical example of the analysis applied for exemplary CA and HS signals.

FIG. 3 illustrates a graphical example of the analysis applied at 204-216 for exemplary CA and HS signals. The HS signals collected and presented in connection with FIG. 3 were collected along the X axis of the accelerometer and filtered utilizing a narrowband filter. In the example of FIG. 3, the CA signals and HS signals are collected for a period of time, such as one minute. An upper panel 302 illustrates the series of HS segments (e.g., 60) of the HS signal aligned with one another over an interval of time. For example, the interval of time may have a duration of 0.8 seconds, where successive HS segments of the HS signal are aligned with one another, beginning at a time zero and ending at a time approximately 0.75 seconds later. Each HS segment is initiated at a time relative to a COI from the CA signals, such as the peak of the R-wave in an EGM signal. Each of the HS segments (e.g., 60 HS segments) are analyzed during separate iterations through the operations of FIG. 2.

The lower panel 304 illustrates an aggregate (e.g., mean) HS segment 306 that is a combination of the series of HS segments and an aggregate (e.g., mean) CA segment 308 over the corresponding series of CA segments. Starting and ending aggregate search window boundaries 310, 312 define an aggregate S1 search window 314, while starting and ending aggregate search window boundaries 316, 318 define an aggregate S2 search window 320. The boundaries 310, 312, 316 and 318 represent a combination (e.g., mean) of individual boundaries identified in connection with each individual HS segment. The starting boundaries 310, 316 for the S1 and S2 search windows 314, 320 are defined in time relative to the COI of the CA signals. An aggregate S1_COM 322 is illustrated within the S1 search window 314. An aggregate S2_COM 324 is illustrated within the S2 search window 320. The S1_COM 322 and S2_COM 324 are formed by combining each of the individual S1_COMs and S2_COMs at 212 (FIG. 2).

Figure 4:
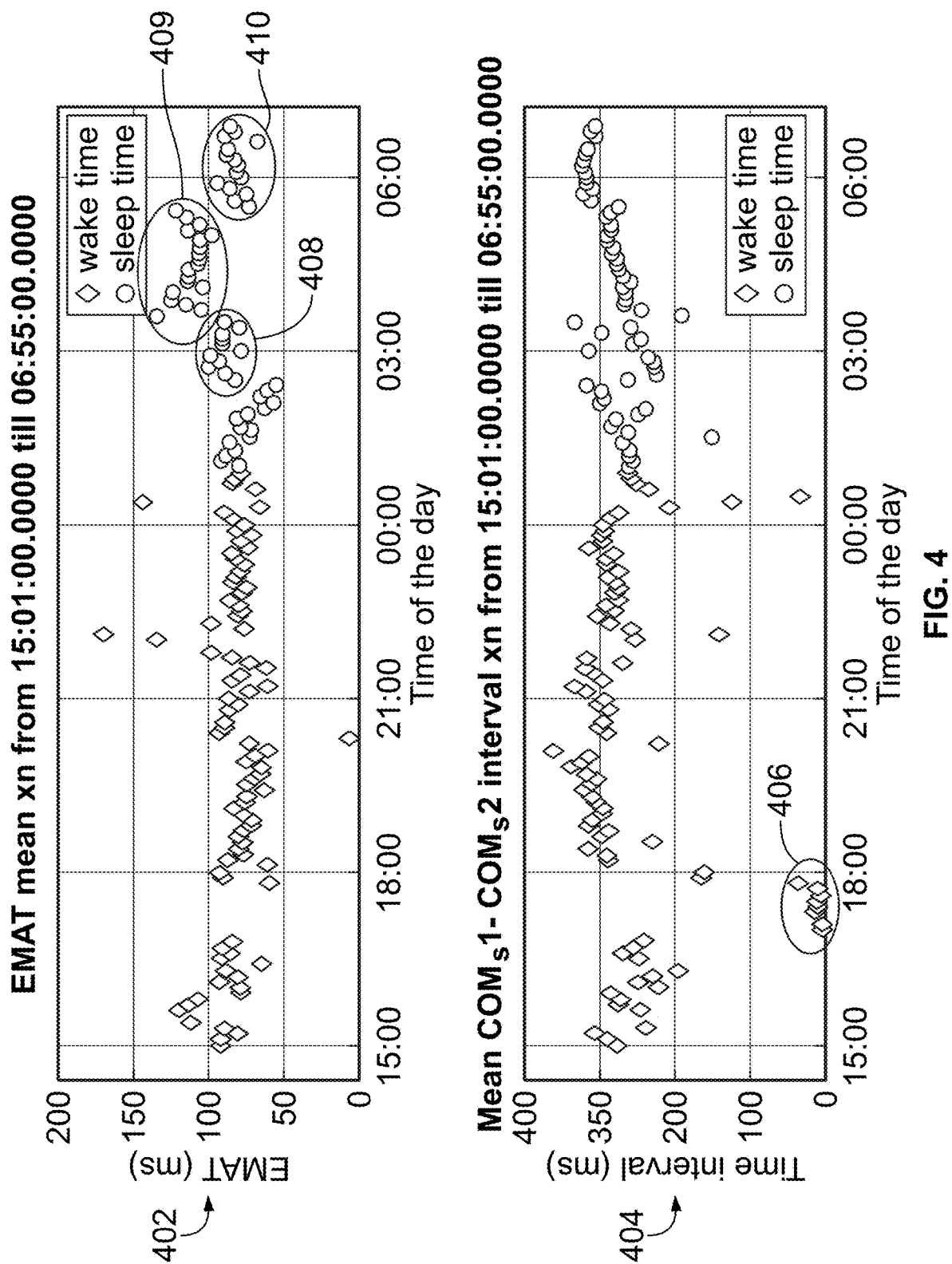
FIG. 4 illustrates an example of a format in which EMAT and SI trend data may be presented.

FIG. 4 illustrates an example of a format in which EMAT and SI trend data may be presented. The EMAT and SI trend data may be presented to a clinician, or other medical personnel, in the manner illustrated in FIG. 4. The EMAT and SI trend data is based on HS signals that were collected along the X axis of the accelerometer and filtered utilizing a narrowband filter. In upper panel 402 presents EMAT trend data by plotting a time of day along the horizontal axis and a measurement for the duration of the EMAT (in milliseconds) along the vertical axis. Each point along the trending graph represents the mean value for the EMAT calculated over a one-minute period of time. The EMAT data is collected and presented over a longer period of time (e.g., an eight-hour interval of time). The EMAT data points from 1500 hrs. to 01:00 represent measurements collected while the patient was awake, while the EMAT data points from 01:00 to 07:00 represent measurements collected while the patient was asleep. As illustrated, a majority of the EMAT data points remain in a relatively narrow range between 50 ms and 130 ms, which may indicate that the patient is experiencing a relatively stable EMAT heart function.

A lower panel 404 presents SI trend data by plotting the same time interval along the horizontal axis and a measurement for the duration of the SI (in milliseconds) along the vertical axis. As noted above in connection with panel 402, each data point along the trending graph represents the mean value for the SI calculated over a one-minute period of time. The SI data is collected and presented over a longer period of time, such as the exemplary eight-hour interval. The SI data points prior to the time 01:00 correspond to when the patient is awake, and the SI data points thereafter correspond to when the patient is asleep. As illustrated, a majority of the SI data points remain in a relatively narrow range between 210 ms and 350 ms, which may indicate that the patient is experiencing a relatively stable EMAT heart function.

Figure 5:
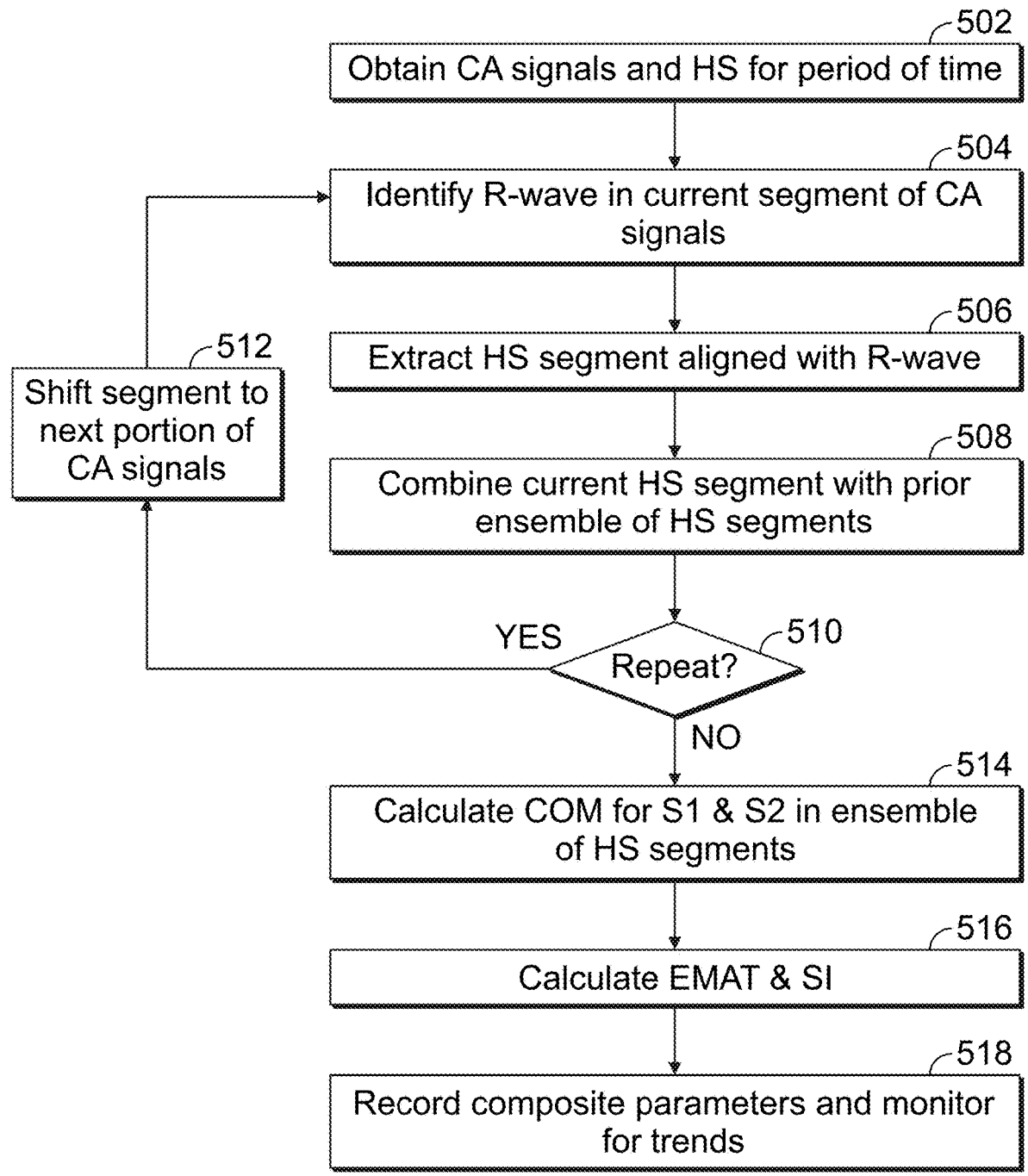
FIG. 5 illustrates a method for monitoring heart function based on heart sounds in accordance with embodiments herein.

FIG. 5 illustrates a method for monitoring heart function based on heart sounds in accordance with embodiments herein. The operations of FIG. 5 may be implemented by hardware, firmware, circuitry and one or more processors housed entirely within an IMD, a local external device or remote server. Optionally, the operations of FIG. 5 may be partially implemented by an IMD and partially implemented by a local external device and/or remote server.

At 502, one or more processors obtain CA signals and HS signals for a common period of time. For example, the period of time may represent a predetermined number of seconds, minutes or otherwise, or alternatively a number of cardiac beats. The CA signals may be sensed utilizing one or more combinations of electrodes and sensing circuitry within or coupled to the IMD. The HS signals may be sensed utilizing a three-dimensional accelerometer and HS filtering circuitry within or coupled to the IMD.

At 504, the one or more processors identify a COI within a current segment of the CA signals. For example, the segment may have a duration approximating the duration of a single heartbeat or some other fixed duration, and the COI may represent the peak of the Q-wave, peak of the R-wave or otherwise.

At 506, the one or more processors overlay S1 and S2 search windows over respective segments of the HS signals where the positions of the S1 and S2 search windows are determined based on the COI from the CA signal segment. For example, when the COI represents the peak of the R-wave, the S1 search window may be positioned to begin at the same time as the R-wave peak or a predetermined first interval before or after the R-wave peak. The S2 search window may then be positioned to begin a predetermined second interval after the R-wave peak and/or a predetermined third interval after the end of the S1 search window. The S1 and S2 search windows each have a corresponding duration that is sufficient to span from prior to a beginning and to extend past an ending of the corresponding S1 and S2 heart sounds. For example, the S1 and S2 search windows may be preprogrammed to be 250 ms each.

At 508, the one or more processors combine the current S1 and S2 HS segments with an aggregate set of previously identified S1 and S2 HS segments. For example, the current S1 HS segment may be averaged with one or more prior S1 HS segments to form a running composite S1 HS segment. Similarly, the current S2 HS segment may be averaged with one or more prior S2 HS segments to form a running composite S2 HS segment. It is recognized that averaging is merely one example of a manner to mathematically combine current and prior HS segments, and other alternative mathematical combinations may be used.

At 510, the one or more processors determine whether to repeat the operations at 504-508. The operations at 504-508 are to be repeated for each segment of the CA signals and a corresponding segment of the HS signals obtained for the select period of time. For example, if the CA and HS signals are recorded at 502 for one minute, and each iteration of 504-508 processed a 60 second segment of the CA and HS signals, the one or more processors would analyze 60 separate combinations of S1 and S2 HS segments, and the operations at 504-508 will be repeated 60 times. Based on the decision at 510, flow branches to 512 or to 514.

At 512, the one or more processors shift the segment to be analyzed to a next portion of the HS and CA signals. For example, when the CA signal segment that is analyzed is one second in length, the segment may be shifted a full one second forward in time such that the next segment does not overlap the prior segment. Alternatively, the segment may be shifted a percentage of the length of the segment (e.g., 25%), such that the next segment partially overlaps the prior segment. Thereafter, the operations at 504-508 are repeated for the next segment of the CA signals and a corresponding next segment of the HS signals. The next R-wave is detected (at 504), which then defines the positions for the next S1 and S2 search windows (at 506). The current S1 and S2 segments are then combined with the S1 and S2 aggregates, such as by maintaining an average or mean S1 data value and S2 data value at each sample point or point in time.

At 510, when the process determines that the entire CA signals and HS signals have been analyzed, flow moves to 514.

At 514, the one or more processors calculate an aggregate center of mass for the ensemble/aggregate collection of S1 segments to obtain a composite S1 COM. The one or more processors also calculate an aggregate center of mass for the ensemble/aggregate collection of S2 segments to obtain a composite S2 COM. The composite S1 COM represents a center of mass for the ensemble of S1 signals across the entire recording period. The composite S2 COM represents a center of mass for the ensemble of S2 signals across the entire recording. The composite S1 COM and S2 COM may utilize the same Equations 1, 2 and 3 as described above in connection with FIG. 2, except that the underlying HS amplitudes utilized represent ensembles/averages at each point across the composite S1 and S2 segments over multiple heart beats and not individual data points for a single heartbeat.

At 516, the one or more processors calculate various indicators of heart function, such as an EMAT and SI utilizing the same Equations 5 and 6 described above, except that the underlying data points represent a composite S1 COM, composite S2 COM and composite R-wave peak over multiple heart beats and not for a single heartbeat.

At 518, the one or more processors store/record the composite parameter values. In addition, at 518, the one or more processors compare the stored composite parameter values to previously stored composite parameter values to monitor for trends.

Figure 6:
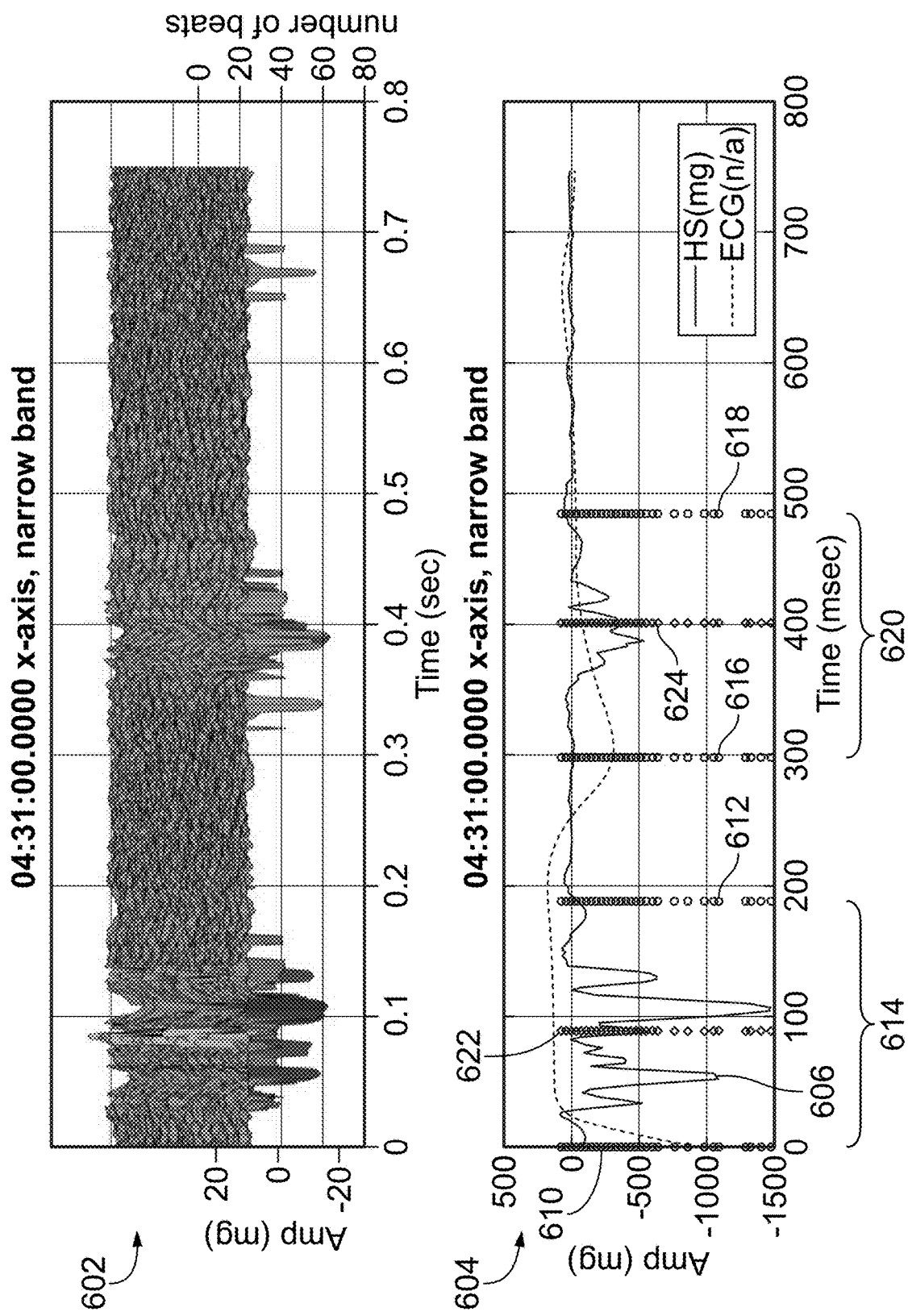
FIG. 6 illustrates a graphical example of the analysis applied in connection with the operations of FIG. 5 for exemplary CA and HS signals.

FIG. 6 illustrates a graphical example of the analysis applied in connection with the operations of FIG. 5 for exemplary CA and HS signals. The HS signals collected and presented in connection with FIG. 5 were collected along the X axis of the accelerometer and filtered utilizing a narrowband filter. Upper panel 602 illustrates the series of HS segments (e.g., 60) of the HS signal aligned with one another over an interval of time, where successive HS segments of the HS signal are aligned with one another, beginning at a time zero and ending at a time approximately 0.75 seconds later.

The lower panel 604 illustrates a composite/aggregate (e.g., mean) HS segment 606 that is a combination of the series of HS segments (generated at 504-512) and an aggregate (e.g., mean) CA segment 608 over the corresponding series of CA segments. Starting and ending aggregate search window boundaries 610, 612 define a composite/aggregate S1 search window 614, while starting and ending aggregate search window boundaries 616, 618 define a composite/aggregate S2 search window 620. The boundaries 610, 612, 616 and 618 represent a combination (e.g., mean) of individual boundaries identified in connection with each individual HS segment. The starting boundaries 610, 616 for the composite S1 and S2 search windows 614, 620 are defined in time relative to the COI of the CA signals (e.g., each individual R-wave or a composite R-wave). An aggregate S1 COM 622 is illustrated within the S1 search window 614. An aggregate S2 COM 624 is illustrated within the S2 search window 620. The composite/aggregate S1 and S2 COMs 622 and 624 are formed by performing single corresponding COM calculations based on the composite/aggregate S1 and S2 segments.

It should be noted that the process of FIG. 2 and results as shown in the lower panel of FIG. 3 are based on the same CA and HS signals as used in the process of FIG. 5 and results as shown in the lower panel of FIG. 6. However, the locations of the search window boundaries differ for the S1 search window and S2 search window. For example, in FIG. 3, the outer boundary 312 for the S1 search window 314 is positioned slightly after the 200 ms time marker, while the outer boundary 612 for the S1 search window 614 is positioned slightly before the 200 ms time marker. Also, the S2 search window 320 in FIG. 3 begins at 330 ms and ends at approximately 540 ms, while the S2 search window 620 begins at 300 ms and ends at approximately 490 ms. Further, the S1 COM and S2 COM calculated based on the process of FIG. 2 also differs from the S1 COM and S2 COM calculated based on the process of FIG. 5. When the COMs are calculated based on the process of FIG. 2, the S1 COM 322 and S2 COM 324 (in FIG. 3) are positioned at the 100 ms and 375 ms time markers. However, when the S1 and S2 COMs are calculated based on the process of FIG. 5, the S1 COM 622 and the S2 COM 624 (in FIG. 5) are positioned at the 90 ms and 400 ms time marker.

Optionally, the calculations of FIGS. 2 and 5 may both be applied, or one may be selected by a physician at the time of implant or during a clinical visit.

Figure 7:
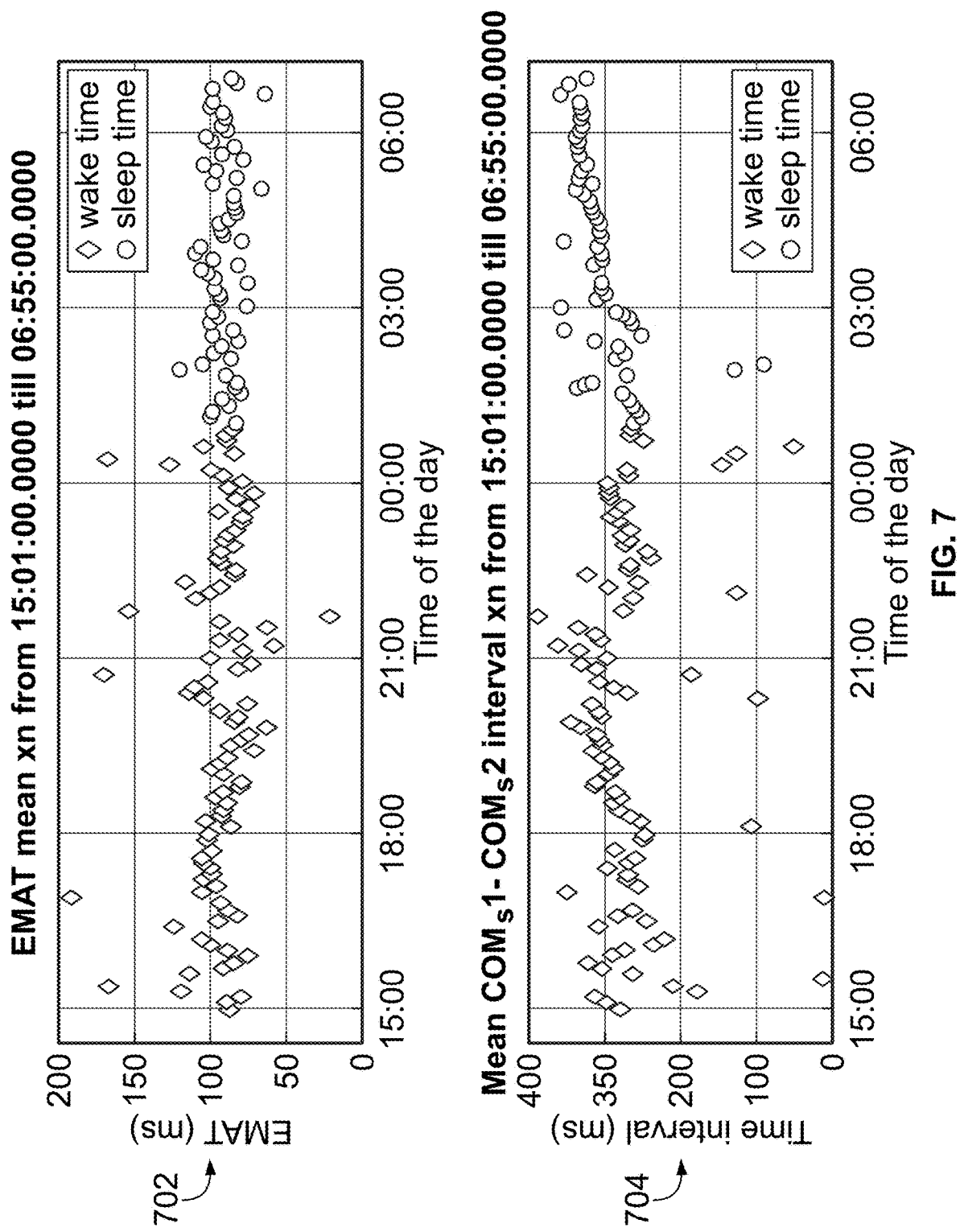
FIG. 7 illustrates an example of the EMAT and SI trend data resulting from the process of FIG. 5.

FIG. 7 illustrates an example of the EMAT and SI trend data resulting from the process of FIG. 5. The EMAT and SI trend data may be presented to a clinician, or other medical personnel, in the manner illustrated in FIG. 7. As discussed above, the upper panel 702 presents EMAT trend data by plotting time of day versus EMAT in milliseconds. The lower panel 704 presents SI trend data by plotting the same time interval along the horizontal axis and a measurement for the duration of the SI (in milliseconds) along the vertical axis.

When the EMAT and SI data distributions are compared between FIGS. 4 and 7, slight differences are noticed. For example, the collection of SI data points at 406 in FIG. 4 are not present in the SI data set presented in FIG. 7. Also, the EMAT data set in FIG. 4 illustrates a division between the groups of data noted at 408-410 while the patient is asleep. However, the EMAT data set in FIG. 7 no longer illustrates such a division while the patient is asleep.

Figure 8:
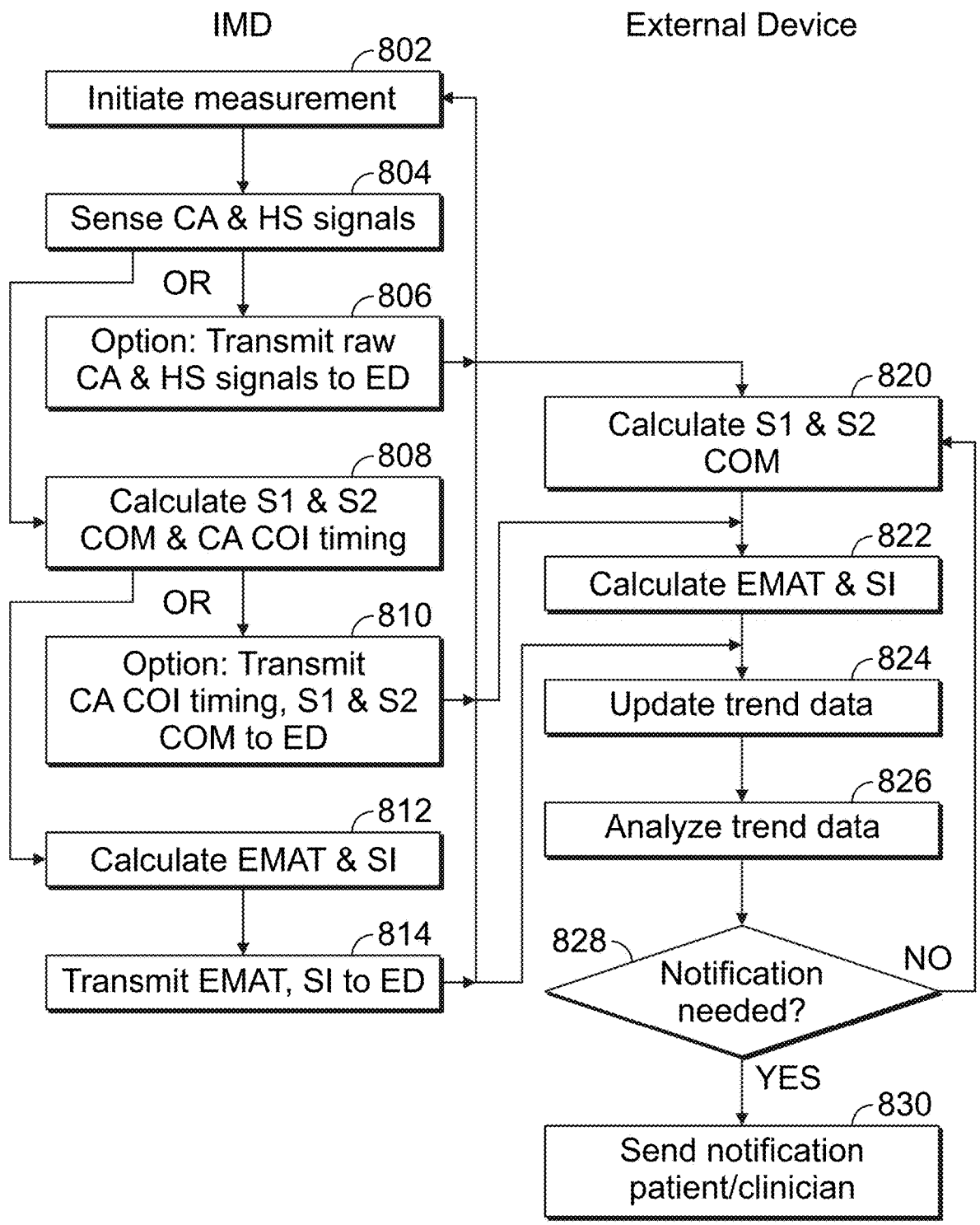
FIG. 8 illustrates an example application that may be implemented in accordance with embodiments herein.

FIG. 8 illustrates an example application that may be implemented in accordance with embodiments herein. The operations along the left side of the flow diagram represent operations that may optionally be performed by an IMD, while the operations along the right side represent operations that may optionally be performed by an external device. The external device may represent a local device and/or a remote external device, such as a server).

At 802, the IMD periodically initiates one or more of the processes described herein to collect CA and HS signals. For example, the IMD may collect CA and HS signals multiple times per day, such as three times per day while a patient is asleep. It is recognized that the IMD may collect CA and HS signals on other periodic or non-periodic bases, as well as based on certain criteria, such as other factors detected by the IMD. For example, the operations of FIG. 8 may be initiated when a patient is experiencing a fast heart rate, when an arrhythmia detection algorithm detects various arrhythmias (e.g., atrial fibrillation, atrial tachycardia, ventricular fibrillation, ventricular tachycardia, bradycardia, sinus pause and the like). Additionally or alternatively, the process may be initiated based on changes in patient posture, changes in activity level, a determination that an IMD has shifted within a subcutaneous pocket and the like. For example, it may be desirable to collect separate trending data sets for different activity levels (e.g., one data set when a patient is at rest, one data set when a patient is exercising). Further, it may be desirable to collect a new trend data set when one or more processors of the IMD determine that the physical position and orientation of the IMD has shifted within a subcutaneous pocket. The determination that the IMD has shifted within the pocket may also warrant initiation of a calibration operation to determine which one or more of the axes of the accelerometer should be utilized to sense the HS signals. For example, at the time of implant, it may be determined to utilize the data collected along the X-axis. However, at a later point in time, the IMD may shift within the subcutaneous pocket, and in response thereto, it may be determined to utilize the data collected along the Y-axis.

Once a measurement operation has been initiated, flow moves to 804 where CA and HS signals are sensed by the corresponding electrodes and accelerometer and corresponding sensing circuitry. Following 804, various options may be implemented. For example, at 806, the IMD may simply transmit the raw CA and HS signals to an external device, such as a patient's phone, clinician programmer, bedside monitor and the like. Additionally or alternatively to transmitting the raw CA and HS signals, flow may return to 802 or continue to 808.

At 808, the one or more processors identify the timing of the COI from the CA signals and calculate S1 and S2 COMs as described herein. The operation at 808 may implement the process of FIG. 2 and/or the process of FIG. 5 and/or various related variations thereto. Once the S1 and S2 COM are determined, various options may be implemented. For example, at 810, the IMD may transmit the COI timing (e.g., the timing of the R-wave peak), along with the S1 and S2 COM to the external device. At this time, the IMD may also transmit the raw CA and HS signals to the external device. Thereafter, flow may return to 802.

Additionally or alternatively, flow may move from 808 and/or from 810 to 812. At 812, the one or more processors of the IMD calculate EMAT and SI data values as described herein in connection with one or both of the processes of FIGS. 2 and 5. At 814, the IMD may transmit the EMAT and SI to the external device and flow returns to 802 to wait for the initiation of the next measurement.

With reference to the operations along the right side of FIG. 8, the external device may perform various combinations of operations based on the information received by the external device. For example, when raw CA and HS signals are transmitted to the external device, at 820, one or more processors of the external device may calculate the S1 and S2 COM utilizing one or both of the processes of FIGS. 2 and 5.

Additionally or alternatively, at 822, one or more processors of the external device may calculate EMAT and SI data values based on COI timing, S1 and S2 values calculated as at 820 and/or received wirelessly from the IMD.

Additionally or alternatively, at 824, one or more processors of the external device may update trend data as described herein. The update to the trend data may be based on calculations performed by the external device at 820 and 822. Additionally or alternatively, the trend data may be updated on EMAT and SI data directly and wirelessly received from the IMD.

At 826, the one or more processors of the external device analyze the trend data. At 828, the one or more processors of the external device determine whether a notification is needed based on the trend data. For example, the trend data may indicate a divergence from a normal pattern. As a non-limiting example, trend data may diverge from a normal pattern when the trend data exceeds or falls below upper and/or lower boundaries, exhibits a change in amplitude of a select amount, exhibits a positive or negative slope that exceeds a threshold and the like. For example, EMAT and/or SI trend data may diverge from prior trends, exceed timing thresholds, or otherwise satisfy criteria established in connection with notifications. When a notification is determined to be needed, flow moves to 830. At 830, the one or more processors of the external device in the notification to the patient, the clinician, the IMD and/or another appropriate destination. When a notification is provided as a communication, the notification may represent in an audio, video, vibratory or other user perceivable medium. The communication may be presented in various formats, such as to display patient information, messages, user directions and the like. The communication is presented on one or more of the various types of electronic devices described herein and may be directed to a patient, a physician, various medical personnel, various patient record management personnel and the like. The communication may represent an identification of a patient diagnosis and various treatment recommendations. The diagnosis and treatment recommendation may be provided directly to the patient. For example, in some circumstances, a diagnosis and treatment recommendation may be to modify a dosage level, in which case, the notification may be provided to the physician or medical practitioner. As another example, the diagnosis and treatment recommendation may be to begin, change or end certain physical activities, in which case, the notification may be provided to the patient, in addition to the physician or medical practitioner. Other nonlimiting examples of a communication type notification include, in part or in whole, a recommendation to schedule an appointment with a physician, schedule an appointment for additional blood work, perform an additional at home point of care blood analysis (e.g., utilizing at home equipment), recommend that the patient collect additional HS and/or IMD data. When a notification includes an action that may be performed by a patient alone, the notification may be communicated directly to the patient. Other nonlimiting examples of a communication type notification include communications sent to a patient (e.g., via an electronic device), where the communication informs the patient of how a patient's lifestyle choices are directly affecting the patient's health. For example, when a patient consumes too much sugar, a notification may be sent to the patient to inform that the excessive sugar has caused a spike or shift in the patient's S1_COM, S2_COM, EMAT, SI and the like. As another example, when a patient avoids exercise for a period of time, the notification may inform a patient that the patient's lack of exercise has raised a S1_COM, S2_COM, EMAT, and/or SI trend.

Figure 9:
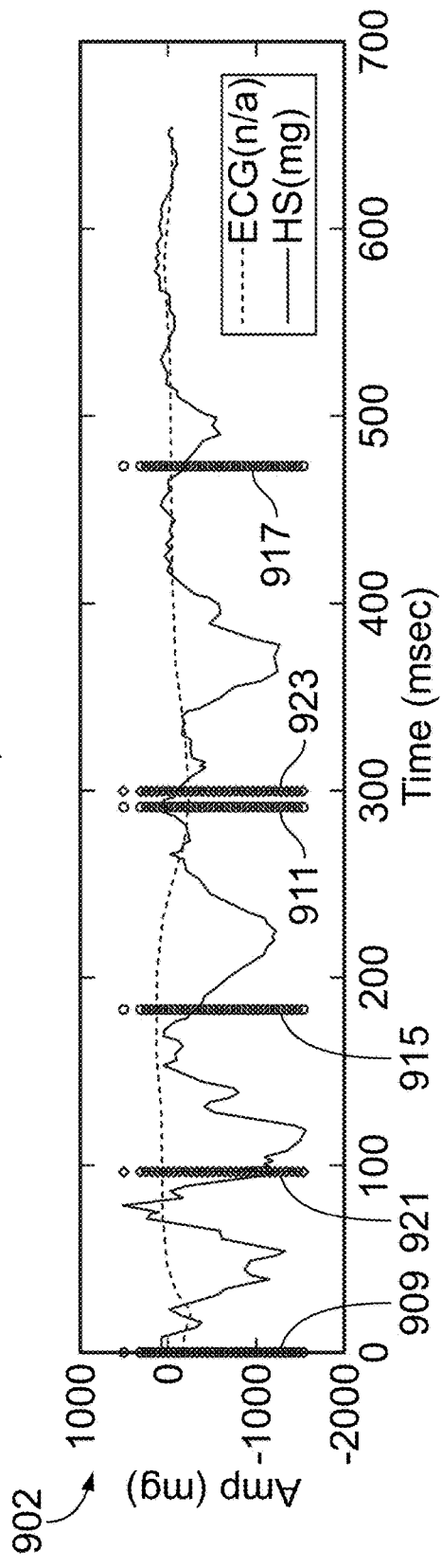
FIG. 9 illustrates a graphical example of the analysis applied in connection with the operations of FIGS. 2 and 5 for exemplary CA and HS signals.
Figure 9:
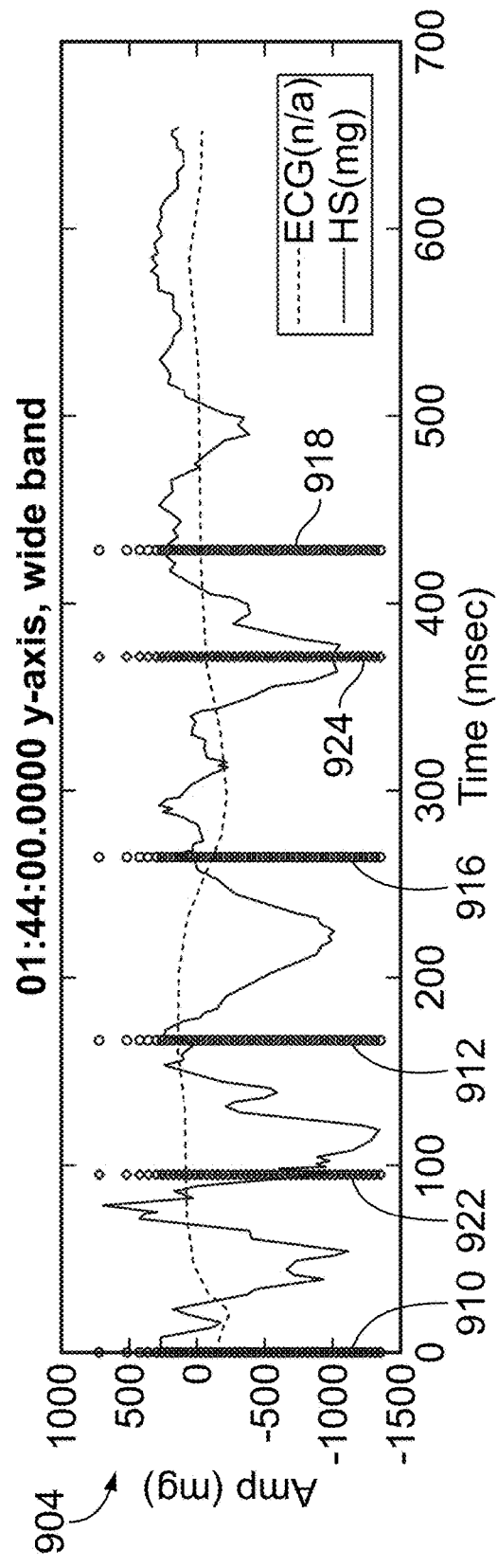

FIG. 9 illustrates a graphical example of the analysis applied in connection with the operations of FIGS. 2 and 5 for exemplary CA and HS signals.

The upper panel 902 illustrates starting and ending search window boundaries 909, 911 define an aggregate S1 search window, while starting and ending aggregate search window boundaries 915, 917 define an aggregate S2 search window. Note that the boundaries 911, 915 of the S1 and S2 search windows overlap. An aggregate/composite S1 COM 921 is illustrated within the S1 search window. An aggregate/composite S2 COM 923 is illustrated within the S2 search window.

The lower panel 904 illustrates a composite/aggregate (e.g., mean) HS segment that is a combination of the series of HS segments (generated at 504-512 in FIG. 5) and an aggregate (e.g., mean) CA segment over the corresponding series of CA segments. Starting and ending aggregate search window boundaries 910, 912 define a composite/aggregate S1 search window, while starting and ending aggregate search window boundaries 916, 918 define a composite/aggregate S2 search window. An aggregate/composite S1 COM 922 is illustrated within the S1 search window. An aggregate/composite S2 COM 924 is illustrated within the S2 search window. The composite/aggregate S1 and S2 COMs 922 and 924 are formed by performing a single corresponding COMs calculation based on the composite/aggregate S1 and S2 segments.

Figure 10A:
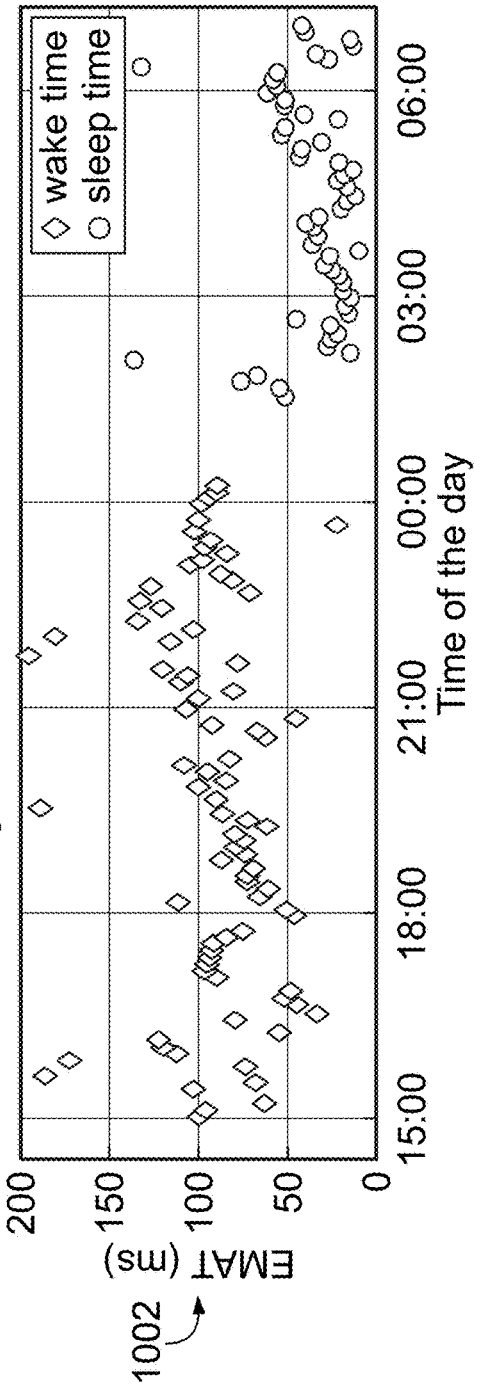
FIG. 10A illustrates EMAT and SI trend data collected based on the S1 and S2 COM of FIG. 9 determined from the y-axis wideband HS signals in accordance with the process of FIG. 2.
Figure 10A:
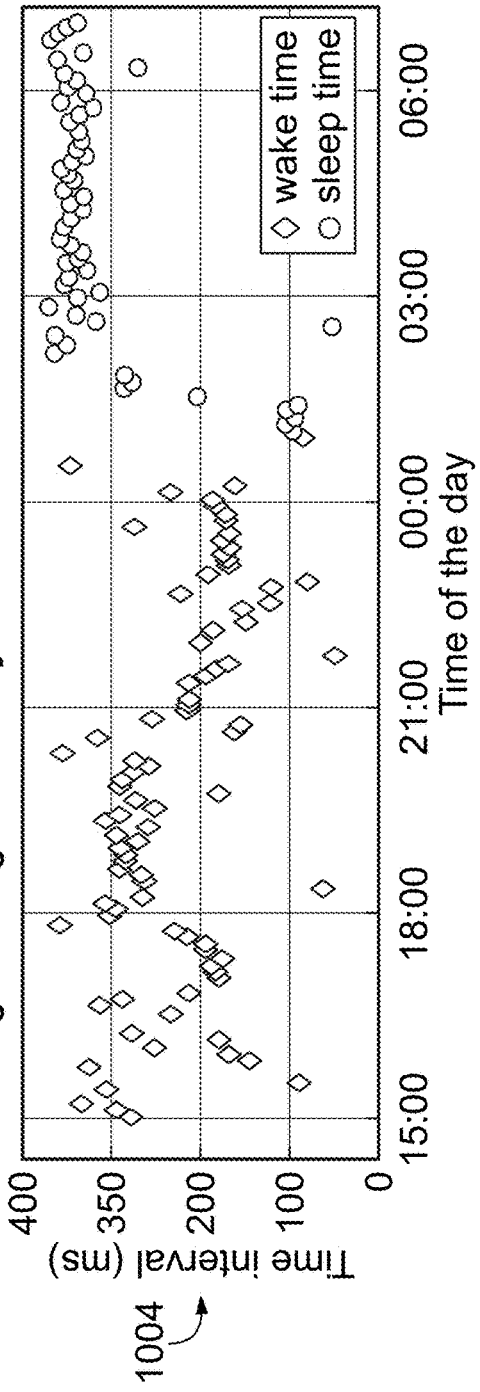
Figure 10B:
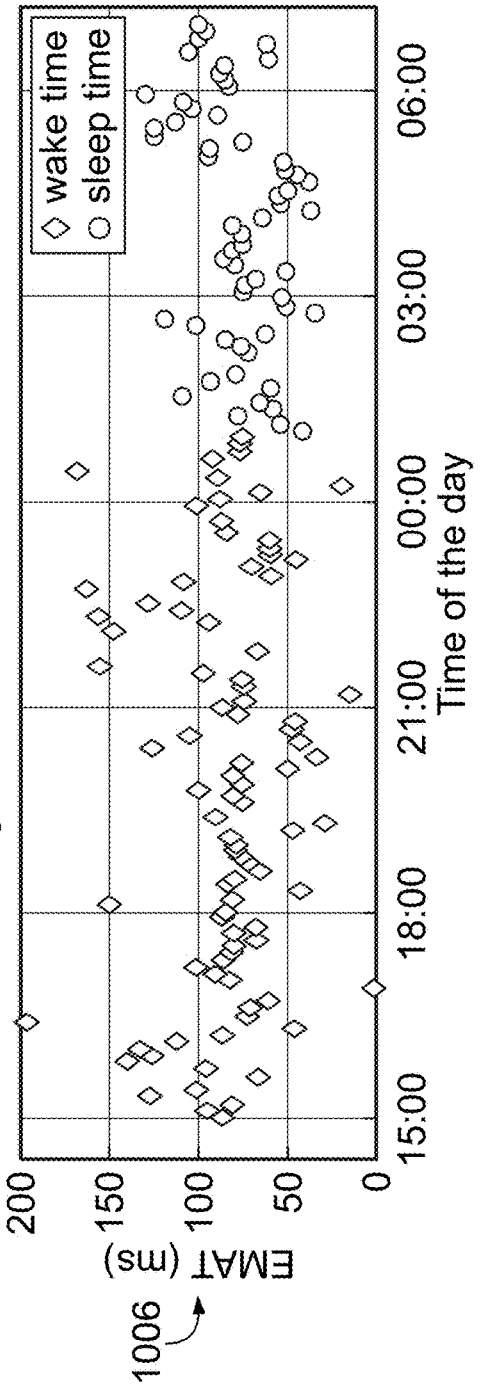
FIG. 10B illustrates EMAT and SI trend data collected based on the S1 and S2 COM of FIG. 9 determined from the y-axis wideband HS signals in accordance with the process of FIG. 5.
Figure 10B:
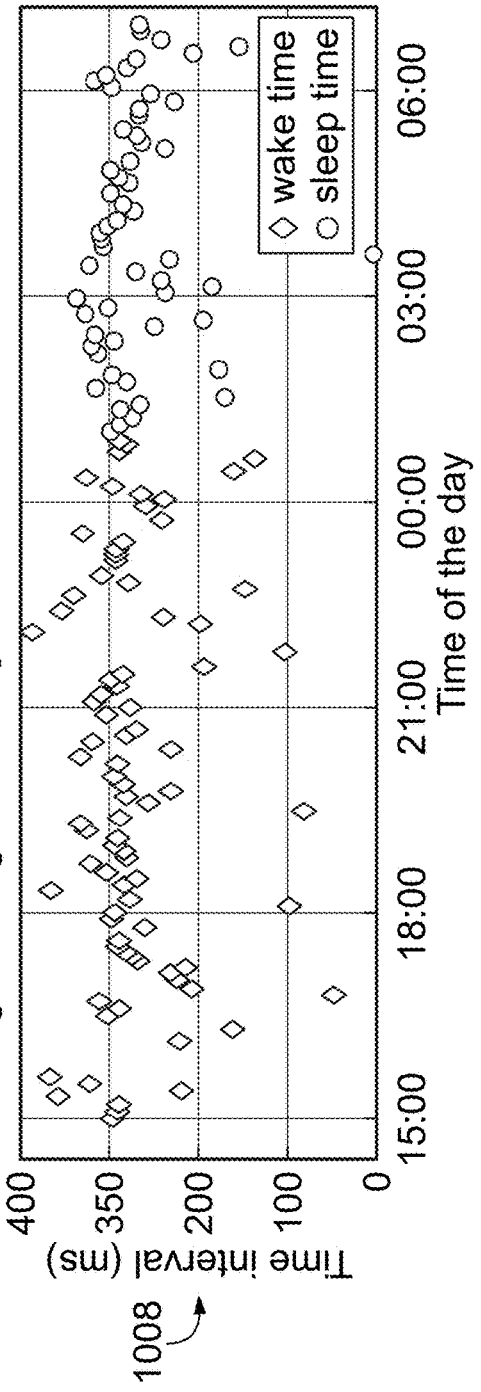

FIGS. 10A and 10B illustrate EMAT and SI trend data collected based on the S1 COM and S2 COM of FIG. 9, where the S1 and S2 COMs were determined from the y-axis wideband HS signals. Panels 1002 and 1004 correspond to trend data calculated in connection with the process of FIG. 2 (also corresponding to the upper panel 902), while panels 1006 and 1008 correspond to trend data calculated in connection with the process of FIG. 5 (also corresponding to the lower panel 904). As the EMAT and SI trend data illustrate, HS signals collected along the y-axis in the present example exhibit a greater distribution as compared to HS signals collected along the X axis (discussed above in connection with FIGS. 4 and 7).

While not directly illustrated, it is recognized that HS signals may also be collected along the z-axis of the accelerometer utilizing a wideband filter, narrowband filter and the like. EMAT and SI trend data may be derived from the HS signals collected along the z-axis, and the distribution thereof analyzed relative to HS signals collected along the y-axis (utilizing various filters) and x-axis (utilizing various filters). The distribution and other features of the EMAT and SI trend data may be reviewed to determine which single axis or combination of axes afford a desired indicator of the corresponding trends.

Optionally, a calibration process may be implemented at the time of implant, during a subsequent clinical visit or automatically/periodically throughout the useful life of the IMD. The calibration process may be utilized to select one or more of the axis specific signals (e.g., the x-axis signal, Y-axis signal or z-axis signal) from the 3-D accelerometer to be used for collecting HS signals. Additionally or alternatively, the calibration process may identify a combination of 2 or more of the axis specific signals to be combined to form the HS signal. For example, a composite HS signal may be formed by summing the HS signals collected along the x-axis and y-axis. An alternative composite HS signal may be formed by summing the HS signals collected along the y-axis and z-axis, or along the x-axis and z-axis, or along all 3 of the X, Y and Z axes. When more than one of the X, Y and Z axes signals are used to form a composite HS signal, each individual axis specific signal represents and HS signal component (e.g., an X axis HS signal component, Y-axis HS signal component and z-axis HS signal component). Additionally or alternatively, when forming a composite HS signal, weights may be applied to each of the X, Y and Z axes HS signal components. For example, the composite HS signal may be formed by multiplying the X axis HS signal component by a first weight W1 and multiplying the Y axis HS signal component by a second weight W2, and then summing the products. The combination of the axis specific signals and the corresponding weights may be determined from one or more calibration operations, such as under direct supervision by a clinician, and/or automatically. The axis specific signal to be utilized, or combination of axis specific signals and weights associated there with may be determined utilizing machine learning.

Implantable Medical Device

Figure 11:
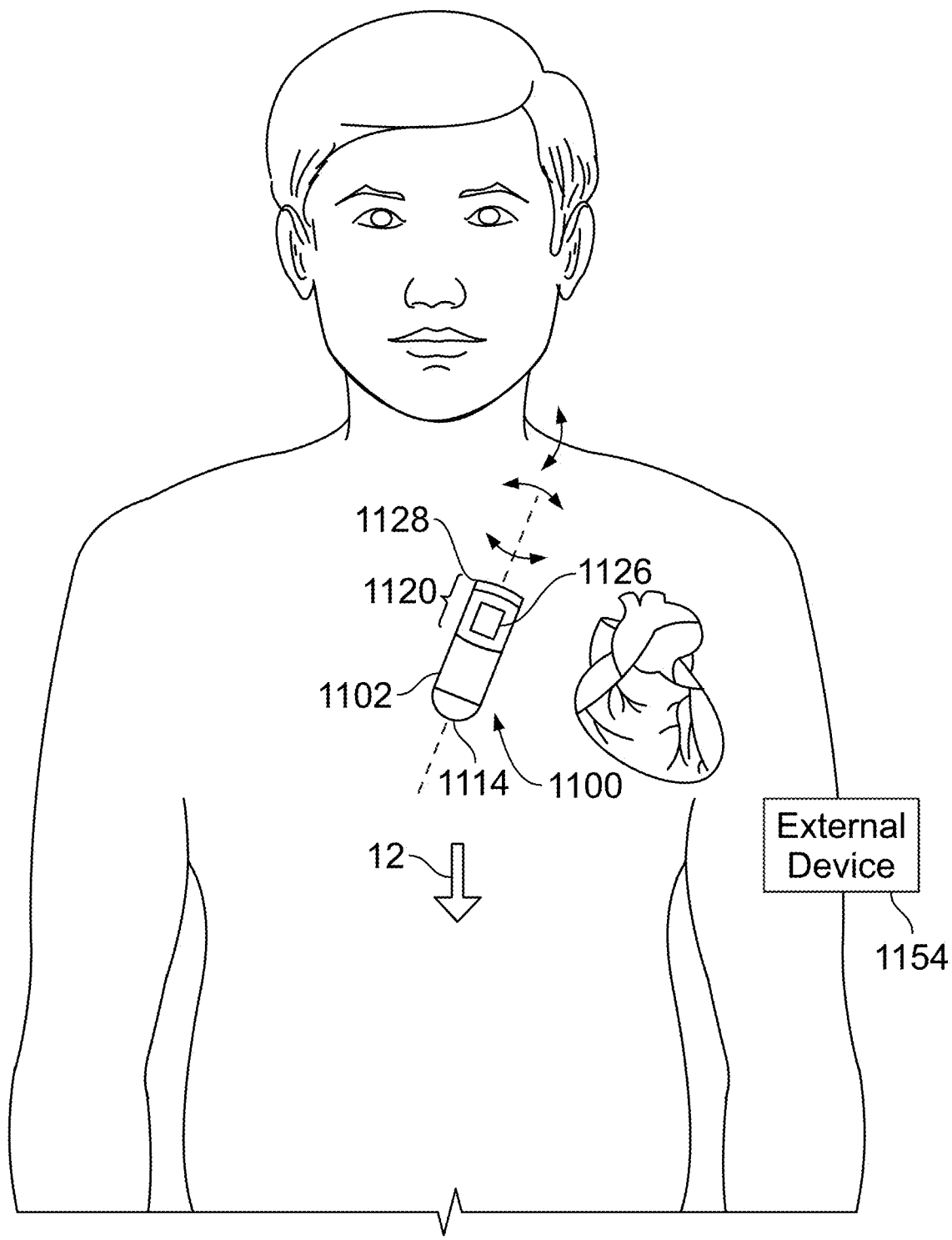
FIG. 11 illustrates an implantable medical device intended for subcutaneous implantation at a site near the heart.

FIG. 11 illustrates an implantable medical device (IMD) 1100 intended for subcutaneous implantation at a site near the heart. The IMD 1100 includes a pair of spaced-apart sense electrodes 1114, 1126 positioned with respect to a housing 1102. The sense electrodes 1114, 1126 provide for detection of far field electrogram signals. Numerous configurations of electrode arrangements are possible. For example, the electrode 1114 may be located on a distal end of the IMD 1100, while the electrode 1126 is located on a proximal side of the IMD 1100. Additionally or alternatively, electrodes 1126 may be located on opposite sides of the IMD 1100, opposite ends or elsewhere. The distal electrode 1114 may be formed as part of the housing 1102, for example, by coating all but a portion of the housing with a nonconductive material such that the uncoated portion forms the electrode 1114. In this case, the electrode 1126 may be electrically isolated from the housing 1102 electrode by placing it on a component separate from the housing 1102, such as the header 1120. Optionally, the header 1120 may be formed as an integral portion of the housing 1102. The header 1120 includes an antenna 1128 and the electrode 1126. The antenna 1128 is configured to wirelessly communicate with an external device 1154 in accordance with one or more predetermined wireless protocols (e.g., Bluetooth, Bluetooth low energy, Wi-Fi, etc.).

The housing 1102 includes various other components such as: sense electronics for receiving signals from the electrodes, a microprocessor for analyzing the far field CA signals, including assessing the presence of R-waves in cardiac beats occurring while the IMD is in different IMD locations relative to gravitational force, a loop memory for temporary storage of CA data, a device memory for long-term storage of CA data, sensors for detecting patient activity, including an accelerometer for detecting acceleration signatures indicative of heart sound, and a battery for powering components.

In at least some embodiments, the IMD 1100 is configured to be placed subcutaneously utilizing a minimally invasive approach. Subcutaneous electrodes are provided on the housing 1102 to simplify the implant procedure and eliminate a need for a transvenous lead system. The sensing electrodes may be located on opposite sides of the device and designed to provide robust episode detection through consistent contact at a sensor-tissue interface. The IMD 1100 may be configured to be activated by the patient or automatically activated, in connection with recording subcutaneous ECG signals.

The IMD 1100 senses far field, subcutaneous CA signals, processes the CA signals to detect arrhythmias and if an arrhythmia is detected, automatically records the CA signals in memory for subsequent transmission to an external device 1154.

The IMD 1100 is implanted in a position and orientation such that, when the patient stands, the IMD 1100 is located at a reference position and orientation with respect to a global coordinate system 110 that is defined relative to a gravitational direction 12. For example, the gravitational direction 12 is along the Z-axis while the X-axis is between the left and right arms.

As explained herein, the IMD 1100 includes electrodes that collect cardiac activity (CA) signals in connection with multiple cardiac beats and in connection with different IMD locations (e.g., different positions and/or different orientations). The IMD 1100 also includes one or more sensors to collect acceleration signatures that are indicative of heart sounds produced at different points in a cardiac cycle.

Figure 12:
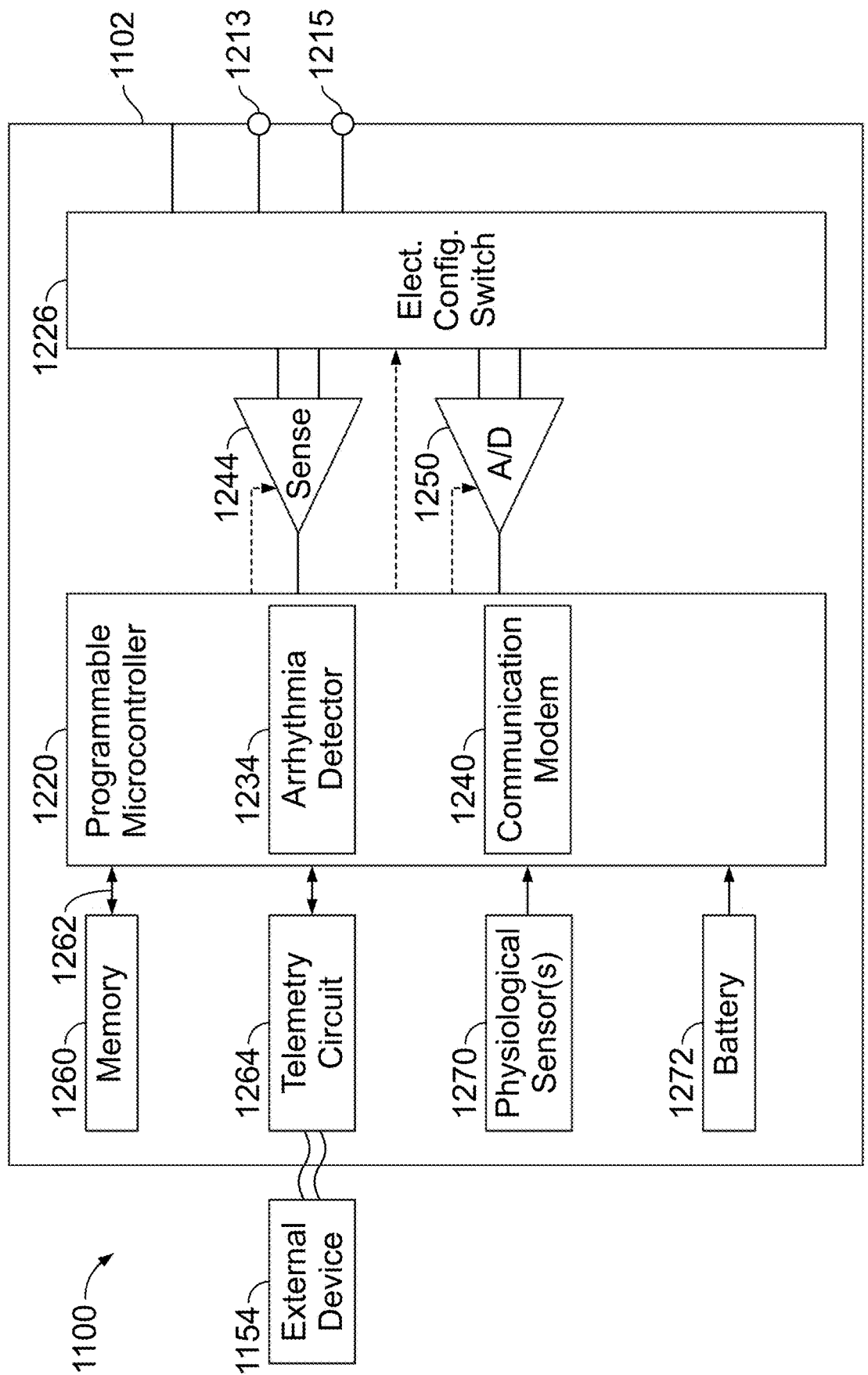
FIG. 12 shows an example block diagram of the IMD 1100 formed in accordance with embodiments herein.

FIG. 12 shows an example block diagram of the IMD 1100 formed in accordance with embodiments herein. The IMD 1100 may be implemented to monitor ventricular activity alone, or both ventricular and atrial activity through sensing circuit. The IMD 1100 has a housing 1102 to hold the electronic/computing components. The housing 1102 (which is often referred to as the "can," "case," "encasing," or "case electrode") may be programmably selected to act as an electrode for certain sensing modes. Housing 1102 further includes a connector (not shown) with at least one terminal 1213 and optionally additional terminals 1215. The terminals 1213, 1215 may be coupled to sensing electrodes that are provided upon or immediately adjacent the housing 1102. Optionally, more than two terminals 1213, 1215 may be provided in order to support more than two sensing electrodes, such as for a bipolar sensing scheme that uses the housing 1102 as a reference electrode. Additionally or alternatively, the terminals 1213, 1215 may be connected to one or more leads having one or more electrodes provided thereon, where the electrodes are located in various locations about the heart. The type and location of each electrode may vary.

The IMD 1100 includes a programmable microcontroller 1220 that controls various operations of the IMD 1100, including cardiac monitoring. Microcontroller 1220 includes a microprocessor (or equivalent control circuitry), RAM and/or ROM memory, logic and timing circuitry, state machine circuitry, and I/O circuitry. Microcontroller 1220 includes an arrhythmia detector 1234 that is configured to analyze the far field cardiac activity signals to identify the existence of an arrhythmia. The microcontroller 1220 also includes arrhythmia determination circuitry 1235 for analyzing the CA signals to assess a presence or absence of R-waves within the cardiac beats from a first segment of the CA signals and detect an arrythmia based on the presence or absence of one or more R-waves from the cardiac beats within a second segment of the CA signals.

The microcontroller 1220 also includes an HS signal analysis (HSA) process 1237. The HSA process 1237 is configured to implement one or more of the operations discussed herein. The HSA process 1237 is configured to be a computer implemented method to identify a characteristic of interest (COI) of a heartbeat from the CA signals, overlay a HS search window onto an HS segment of the HS signals based on the COI from the CA signals, calculate a center of mass (COM) for at least one of S1 or S2 HS based on the HS segment of the HS signals within the search window to obtain a corresponding at least one of S1 COM or S2 COM, and calculate at least one of EMAT or SI data values based on the at least one of S1 COM or S2 COM. The microcontroller 1220 records at least one of the EMAT or SI data over time to form an EMA T trend and in SI trend.

As explained herein, the HSA process 1237 is configured to overlay the S1 and S2 search windows over corresponding HS segments. The HSA process 1237 is configured to align the S1 search window over the HS signals to begin at or near an R-wave peak, the R-wave peak representing the COI. The HSA process 1237 is configured to align the S2 search window over the HS signals to begin a predetermined interval after one of an end of the S1 search window or an R-wave peak, the R-wave peak representing the COI. The HSA process 1237 is configured to calculate the S1 COM by: calculating products of i) amplitudes of the HS signals at points along the S1 search window and ii) positions of the corresponding points along the S1 search window; summing the products to form a first sum; summing the amplitudes of the HS signals at the points to form a second sum; and dividing the first sum by the second sum. As explained herein, the S1 COM and S2 COM represent corresponding points in time along the CA and HS signals. The COI occurs at a COI point in time along the CA signals, the one or more processors configured to calculate the EMAT by subtracting the S1 COM from the COI point in time. The HSA process 1237 is configured to calculate the SI as a difference between the S1 COM and the S2 COM.

In accordance with embodiments herein, the microcontroller 1220 manages storage of the EMAT and SI over a period of time and monitors an EMAT trend and an SI trend over period of time for an indication of a change in a physiologic or non-physiologic condition. For example, the microcontroller 1220, also referred to as an IMD processor, may be configured to perform all or more than one of the identify, overlay or calculate operations. The external device 1154 is configured to wireless communicate with the IMD 1100. The external device 1154 includes ED memory and one or more ED processors. The one or more ED processors may be configured to perform at least one of the identify, overlay and calculate operations. As one example, the external device 1154 may wirelessly receive the CA and HS signals, and the one or more ED processors may perform the identify, overlay and both calculate operations.

Although not shown, the microcontroller 1220 may further include other dedicated circuitry and/or firmware/software components that assist in monitoring various conditions of the patient's heart and managing pacing therapies. A switch 1226 is optionally provided to allow selection of different electrode configurations under the control of the microcontroller 1220. The switch 1226 is controlled by a control signal 1228 from the microcontroller 1220. The IMD 1100 may be further equipped with a communication modem (modulator/demodulator) 1240 to enable wireless communication. In one implementation, the communication modem 1240 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 1240 may be implemented in hardware as part of the microcontroller 1220, or as software/firmware instructions programmed into and executed by the microcontroller 1220. Alternatively, the modem 1240 may reside separately from the microcontroller as a standalone component. The modem 1240 facilitates data retrieval from a remote monitoring network. The modem 1240 enables timely and accurate data transfer directly from the patient to an electronic device utilized by a physician.

The IMD 1100 includes sensing circuit 1244 selectively coupled to one or more electrodes that perform sensing operations through the switch 1226 to detect CA data indicative of cardiac activity. The sensing circuit 1244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 1226 may be used to determine the sensing polarity of the CA signal by selectively closing the appropriate switches. The IMD 1100 further includes an analog-to-digital A/D data acquisition system (DAS) 1250 coupled to one or more electrodes via the switch 1226 to sample CA signals across any pair of desired electrodes. The HSA process 1237 may be applied to signals from the sensing circuit 1244 and/or the DAS 1250.

By way of example, the external device 1154 may represent a bedside monitor installed in a patient's home and utilized to communicate with the IMD 1100 while the patient is at home, in bed or asleep. The external device 1154 may be a programmer used in the clinic to interrogate the IMD 1100, retrieve data and program detection criteria and other features. The external device 1154 may be a handheld device (e.g., smartphone, tablet device, laptop computer, smartwatch and the like) that may be coupled over a network (e.g., the Internet) to a remote monitoring service, medical network and the like. The external device 1154 may communicate with a telemetry circuit 1264 of the IMD through a communication link 1266. The external device 1154 facilitates access by physicians to patient data as well as permitting the physician to review real-time CA signals while collected by the IMD 1100.

The microcontroller 1220 is coupled to a memory 1260 by a suitable data/address bus 1262. The memory 1260 stores the motion data, baseline motion data sets, CA signals, as well as the markers and other data content associated with detection and determination of the arrhythmia.

The IMD 1100 may further include one or more physiologic sensors 1270. For example, the physiologic sensor 1270 may represent one or more accelerometers, such as a three-dimensional (3D) accelerometer. The sensor 1270 may utilize a piezoelectric, a piezoresistive, and/or capacitive components are commonly used to convert the mechanical motion of the 3D accelerometer into an electrical signal received by the microcontroller 1220. By way of example, the 3-D accelerometer may generate three electrical signals indicative of motion in three corresponding directions, namely X, Y and Z directions. The electrical signals associated with each of the three directional components may be divided into different frequency components to obtain different types of information therefrom.

The physiologic sensor 1270 collects device location information with respect to gravitational force while the IMD 1100 collects CA signals in connection with multiple cardiac beats. While shown as being included within the housing 1102, the physiologic sensor(s) 1270 may be external to the housing 1102, yet still, be implanted within or carried by the patient.

Figure 13:
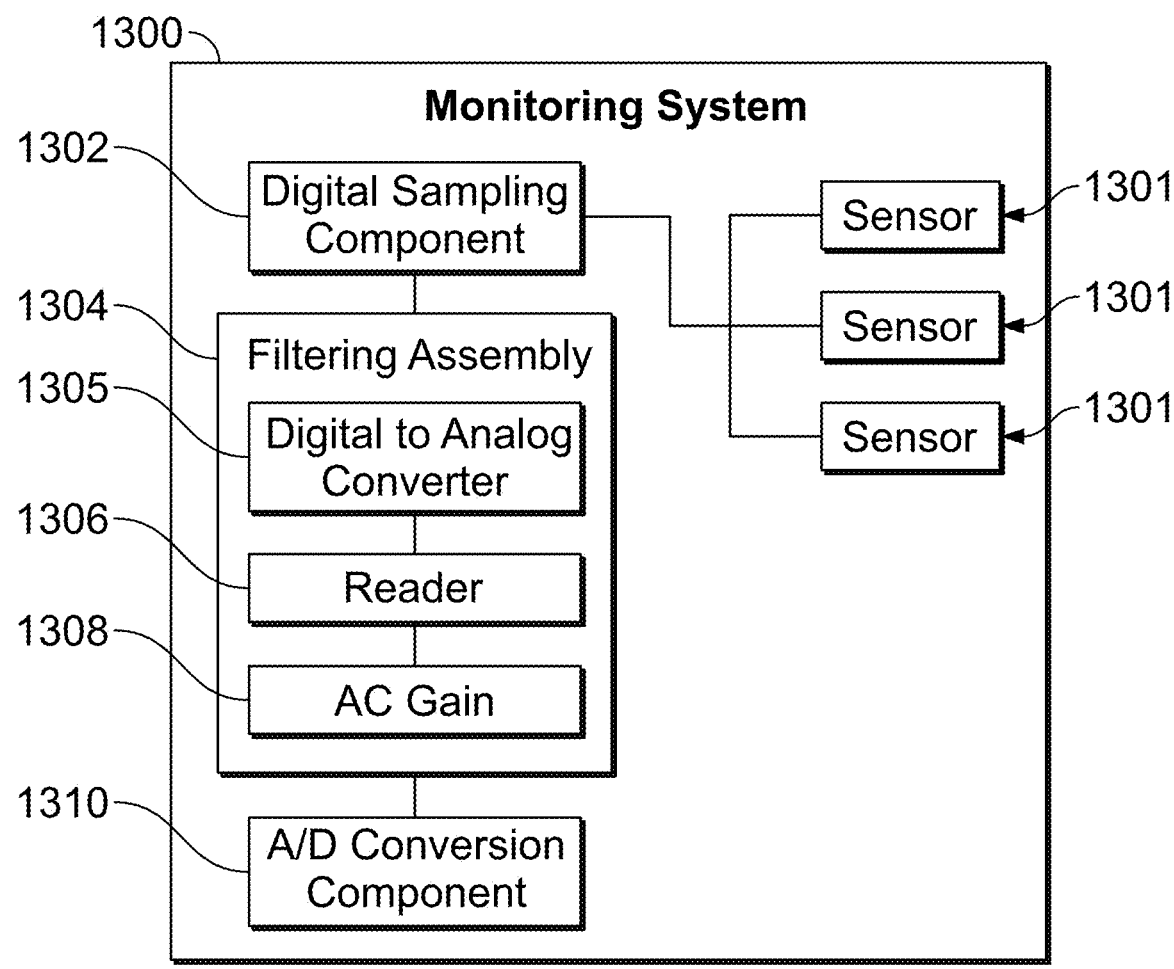
FIG. 13 illustrates a schematic diagram of a physiologic sensor implemented as an accelerometer in accordance with embodiments herein.

FIG. 13 illustrates a schematic diagram of a physiologic sensor (e.g., such as physiologic sensor 1270) that may be implemented as an accelerometer, more generally referred to herein as a monitoring system 1300. The monitoring system 1300 is used to detect and determine heart sound signals. In one embodiment, the monitoring system 1300 is a three-dimensional accelerometer that may be implemented as a chip for placement in an IMD. In another embodiment, the accelerometer is formed and operates in the manner described in U.S. Pat. No. 6,937,900, titled "AC/DC Multi-Axis Accelerometer For Determining A Patient Activity And Body Position," the complete subject matter which is expressly incorporated herein by reference. In yet another embodiment, the accelerometer is formed and operates in the manner described in U.S. Provisional Patent Application 63/021,775, titled Method and System for Heart Condition Detection Using an Accelerometer, the complete subject matter which is expressly incorporated herein by reference. The accelerometer includes sensors that generate first (X), second (Y) and third (Z) accelerometer signals along corresponding X, Y and Z axes (also referred to as first axis accelerometer or HS signals, second axis accelerometer or HS signals and third axis accelerometer or HS signals). The X, Y and Z axes accelerometer signals collectively define a three-dimensional, or multi-dimensional (MD) accelerometer or HS data set. While examples herein are described in connection with an accelerometer that generates accelerometer signals along three orthogonal axes, it is recognized that embodiments may be implemented wherein accelerometer signals are generated along two or more axes, including more than three axes.

The monitoring system 1300 may include sensors 1301 that monitor and receive signals from the X, Y and Z axes. In one embodiment, the individual X, Y and Z signals are received by a digital sampling component 1302 that receives a digital input. Coupled to the digital sampling component 1302 is a filtering assembly 1104 that may include a digital to analog converter 1305 to form an alternating current (AC) signal, a reader device 1306, and an AC gain device 1108. While in this embodiment, the filtering assembly includes the devices provided, in other examples, other devices may be utilized to filter the digital input signal for processing.

The monitoring system 1300 may also include an analog to digital conversion component 1310, along with a position, or direct current (DC) component. In one example, the analog to digital conversion component may be a 13-bit analog to digital converter (ADC). The evaluation version of the monitoring system 1100 may provide 3-axis (X and Y along the chip, Z normal to the chip) DC-coupled posture signal corresponding to 3 orthogonal directions as well as 3-axis AC-coupled activity signal. In one embodiment, each of the 6 signal may be sampled at 100 Hz and accumulated over 1 sec for a total of 12 signals ([X/Y/Z], [posture/activity], [100/1 Hz]). This MD accelerometer data may be used to describe embodiments herein.

While described as a digital signal in relation to FIG. 13, in other embodiments the signal may be an analog signal, filtered, amplified, etc. The accelerometer data signals may be recorded in a data storage of the accelerometer, of an IMD, of a remote device etc. Alternatively, the accelerometer data set may be obtained from a remote device or received from a storage device coupled to the accelerometer. To this end, the accelerometer data set may be a multi-dimensional accelerometer data set.

One or more embodiments generally relate to leadless IMDs and systems, such as pacemakers, implantable cardioverter-defibrillators, cardiac rhythm therapy devices and the like. As explained hereafter, embodiments utilize heart sounds to calculate one or more heart function (HF) indicators for an individual patient and to use the HF indicators to determine one or more therapy related (TR) delays and/or sensing related blanking intervals (SR BIs).

Figure 14:
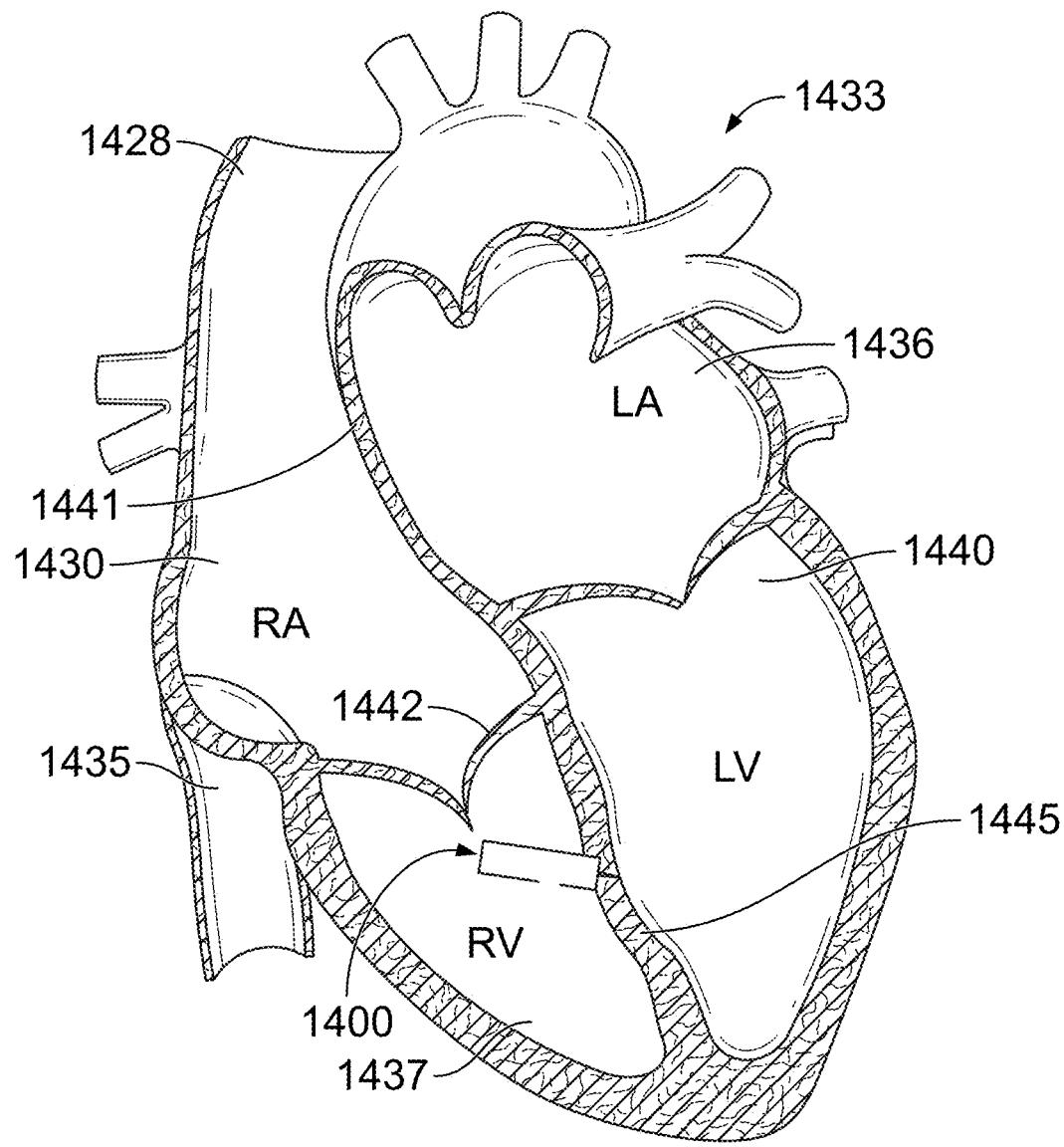
FIG. 14 provides a sectional view of a patient's heart and shows a leadless implantable medical in accordance with embodiments herein.

FIG. 14 provides a sectional view of a patient's heart 1433 and shows a leadless implantable medical device (IMD) 1400. The IMD 1400 has been placed through the superior vena cava 1428 into the right atrium 1430 of the heart 1433. FIG. 14 also shows the inferior vena cava 1435, the left atrium 1436, the right ventricle 1437, the left ventricle 1440, the atrial septum 1441 that divides the two atria 1430, 1436, and the tricuspid valve 1442 between the right atrium 1430 and the right ventricle 1437.

The IMD 1400 is formed in accordance with an embodiment. The IMD 1400 may represent a pacemaker, a cardiac resynchronization therapy (CRT) device, a cardioverter, a cardiac rhythm management (CRM) device, a defibrillator, or the like. The IMD 1400 comprises a housing 1402 configured to be implanted entirely within a single local chamber of the heart 1433, such as entirely and solely within the right atrium 1430, left atrium 1436, the right ventricle 1437 or the left ventricle 1440, for example. Optionally, the IMD 1400 may be implanted outside of the chambers of the heart but located in a vessel proximate to, or attached to an exterior wall of, the heart proximate to the RA, LA, RV or LV.

The chamber in which the IMD 1400 is implanted in (or closest proximally to) is referred to as the "local" chamber. The local chamber includes a local chamber wall that is physiologically responsive to local activation events originating in the local chamber. The local chamber is at least partially surrounded by local wall tissue that forms, contains, or constitutes at least part of a conduction network for the associated chamber.

As shown in FIG. 14, the local chamber in which the IMD 1400 is implanted is the right ventricle 1437. For example, the IMD 1400 is mounted or fixated to the tissue wall of the right ventricle 1437 along the septum 1445 that divides the right ventricle 1437 from the left ventricle 1440. The septum 1445 wall tissue in the right ventricle 1437 may behave physiologically differently than the non-septum ventricular wall tissue. Optionally, the IMD 1400 may be implanted in other regions of the RV, in other chambers of the heart, in vessels along an exterior of a local chamber or implanted in the exterior wall of the heart proximate to a local chamber (e.g, through the epicardium and into the myocardium). FIG. 14 shows the IMD 1400 in the septal wall of the RV, but optionally, the IMD 1400 may be implanted at a higher location proximate to the HIS bundle in the RV. Optionally, the IMD 1400 may be implanted in the RA or elsewhere. Alternatively, multiple IMDs may be implanted into the patient's heart 1433 within different chambers or different segments of the same chamber.

The leadless IMD 1400 may sense for various intrinsic events and delivery corresponding therapies depending upon whether a subsequent intrinsic event is detected within a certain time period. For example, the IMD may utilize one or more atrial-ventricular (AV) delays to manage ventricular pacing in the event an intrinsic ventricular event does not occur within a programmed time period following a preceding intrinsic (or paced) atrial event. Similarly, the IMD may utilize one or more ventricular-ventricular (VV) delays to manage synchronization between right and left side ventricular activity. For example, a leadless IMD in the RV may deliver a paced event when an intrinsic right side ventricular event does not occur within a programmed time period following a preceding intrinsic (or paced) ventricular event in the left ventricular chamber, or vice versa. As another example, the IMD may utilize one or more atrial-HIS (AH) delays to manage HIS bundle pacing in the event an intrinsic event does not occur at the HIS bundle within a programmed time period following a preceding intrinsic (or paced) atrial event. As another example, when the IMD is implanted in the atrium, the IMD may utilize one or more post ventricular atrial refractory period (PVARP) blanking intervals to manage blanking for a sensing circuit following a preceding intrinsic ventricular event.

As explained herein, the leadless IMD "listens" for and detects intrinsic events based on one or more heart sounds of interest. The HS of interest is used to start one or more TR delays and/or SR blanking intervals. The TR delay and/or SR blanking interval is calculated in part based on COM calculations for one or more heart sounds.

Figure 15:
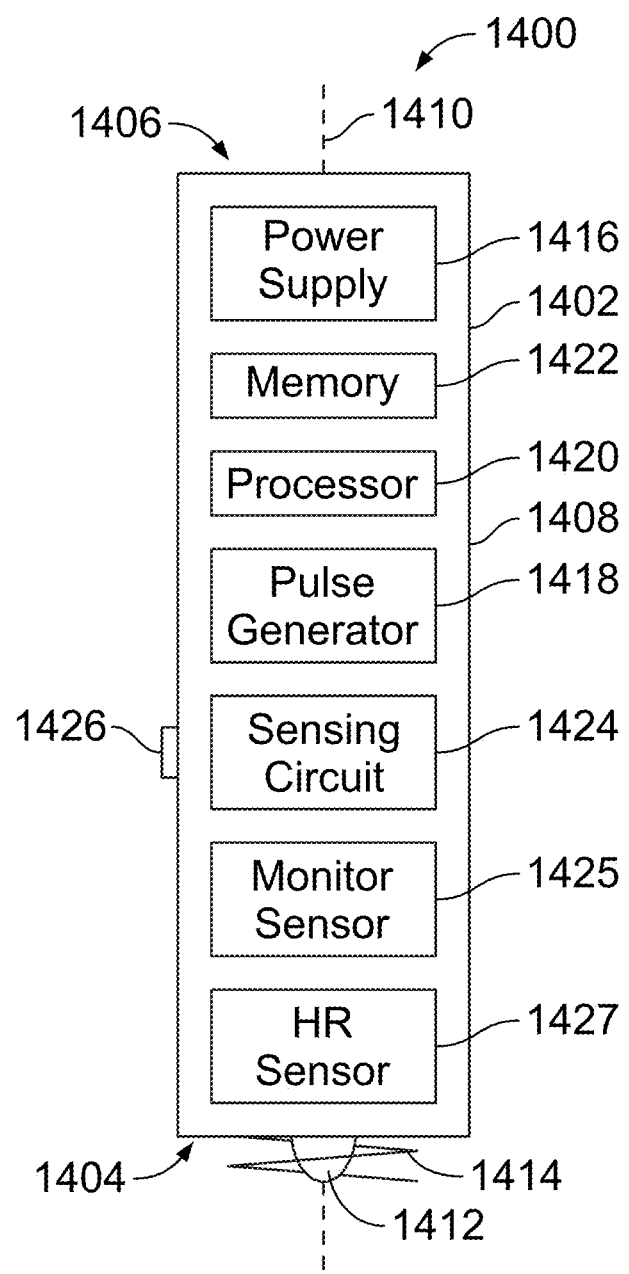
FIG. 15 illustrates a side view of the IMD according to an embodiment.

FIG. 15 illustrates a side view of the IMD 1400 according to an embodiment. The illustrated IMD 1400 includes a schematic representation of some internal components of the IMD 1400. The housing 1402 of the IMD 1400 includes a first mounting end 1404, an opposite second end 1406, and an intermediate shell 1408 extending between the first end 1404 and the second end 1406. The shell 1408 is elongated and tubular in shape and extends along a longitudinal axis 1410. The mounting end 1404 mounts to tissue of an intra-cardiac wall within a chamber of the heart.

The mounting end 1404 includes an electrode 1412 securely attached thereto and projecting outward from the mounting end 1404. The shell 1408 includes one or more electrodes 1426 provided therein remote from the electrode 1412. The electrodes 1412 and 1426 cooperate to define a sensing vector and to sense local CA signals. The electrodes 1412 ad 1426 are further configured to deliver stimulation energy to tissue of interest. As used herein, "tissue of interest" refers to intra-cardiac tissue that the IMD 1400 is configured to monitor and provide stimulation energy. In the illustrated embodiment, the IMD 1400 is configured to be affixed directly to the tissue of interest, as described below. The electrode 1412 may be a cathode electrode that is actively fixated to the myocardium, while the electrode 1426 is an anode electrode. The stimulation energy may be in the form of low-energy pacing pulses, higher-energy shocking pulses, or the like.

When the mounting end 1404 is mounted to the intra-cardiac tissue, the electrode 1412 is securely affixed to and engages the tissue of interest in order to deliver the stimulation energy directly thereto. In addition to delivering stimulation energy, in an alternative embodiment the electrode 1412 may be used to sense electrical activity from the tissue of interest. The electrode 1412 may be formed as a single conductive bulb or, alternatively, as a cone, a single wire, or the like. Optionally, the electrode 1412 is not covered with insulation material and the conductive material is exposed in order to facilitate a good electrical connection to the local wall tissue. Alternatively, at least a portion of the electrode 1412 is covered with insulation to prevent electrical conduction to tissue that engages the insulation.

The mounting end 1404 includes a fixation element to secure the IMD in or proximate to a local chamber of the heart. For example, the fixation element may be a fixation screw 1414 securely attached thereto and projecting outward from the mounting end 104. The fixation screw 1414 is configured to extend into the tissue of interest to anchor the IMD 1400 to the intra-cardiac tissue. The fixation screw 1414 is configured to be screwed into the tissue to firmly adhere the IMD 1400 thereto by pressing the mounting end 1404 against the tissue and rotating the IMD 1400 in a first, coupling direction. The fixation screw 1414 may be extracted from the tissue by rotating the IMD 1400 in an opposite, uncoupling direction in conjunction with a slight tugging force directed away from the myocardial wall. The fixation screw 1414 may be shaped as a helical corkscrew that defines a center channel. For example, the fixation screw 1414 may surround the electrode 1412 such that the electrode 1412 is within the center channel. In an alternative embodiment, the fixation screw 1414 is part of the electrode 1412. For example, the electrode 1412 may have helical threads on an outer surface of the electrode 1412, such that the electrode 1412 forms the fixation screw 1414.

Additionally or alternatively, the fixation element may include one or more loops, tabs and the like that are configured to retain the IMD in a vessel, septal wall or other tissue proximate to the local chamber of the heart. For example, the IMD and/or fixation element may be formed as described in one or more of U.S. Published Application 2019/0099087, publishing Apr. 4, 2019, and titled "Wireless Sensor for Measuring Pressure"; U.S. Pat. No. 9,993,167, issuing Jun. 12, 2018 and titled "Apparatus and Method for Sensor Deployment and Fixation"; U.S. Published Application 2016/0007924, publishing Jan. 14, 2016, and titled "Implantable Pressure Transducer System Optimized to Correct Environmental Factors", the complete subject matter of which is expressly incorporated herein in its entirety.

The housing 102 retains a power supply 1416 and various electronic components that receive electrical current from the power supply 1416. The electronic components provide the functionality of the IMD 1400, such as controlling the stimulation energy delivered to the electrode 1412 and sensing the depolarization along the tissue of interest in response to a pacing pulse or to an intrinsic heartbeat. The power supply 1416 stores charge for gradual disbursal to the electronic components as needed. The power supply 1416 may be a battery. The power supply 1416 has a fixed amount of charge at full capacity. The power supply 1416 may be rechargeable in some embodiments and may not be rechargeable in other embodiments. The power supply 1416 is fully retained within and surrounded by the housing 1402.

The electronic components include a pulse generator 1418, a processor 1420, a memory 1422, a sensing circuit 1424 and a monitoring senor/system 1425, such as monitoring system 1300 (FIG. 13) and/or physiologic sensor 1270 (FIG. 12). The illustration is intended as an overview of the electronic components only, and the electronic components according to an embodiment of the IMD 1400. The pulse generator 1418 provides stimulation energy to the electrode 1412 which is delivered to the tissue of interest that the electrode 1412 engages. The pulse generator 1418 includes circuitry to control the output of stimulation energy directed to the electrode 1412. For example, the pulse generator 1418 produces lower energy pulses for pacing and higher energy pulses for shocking.

The processor 1420 is a controller that controls the flow of charge between the power supply 1416, the electronic components (such as the pulse generator 1418, monitoring sensor 1425 and the sensing circuit 1424), and the electrodes (such as electrode 1412). For example, the processor 1420 controls the timing and intensity or magnitude of the stimulation pulses. If multiple electrodes are used to deliver stimulation energy to the intra-cardiac tissue, the processor 1420 may synchronize the delivery of the pulses. The processor 1420 is communicatively coupled to the pulse generator 1418, the sensing circuit 1424, the memory 1422, and the power supply 1416. The processor 120 also functions based on instructions stored locally in the memory 1422. The memory 1422 is a non-transitory tangible computer readable storage medium. The memory 1422 stores programmable and executable instructions for the processor 1420. The processor 1420 is responsive to the programmable instructions to control operation of the IMD 1400 as described herein. The memory 1422 may also store data. Some of the data may be stored prior to completing assembly of the IMD 1400, while other data may be stored during use of the implanted IMD 1400. For example, the memory 1422 may be used to store data on intrinsic electrical activity within the heart as monitored by the sensing circuit 1424, data on the number, time, and/or magnitude of pacing pulses generated by the pulse generator 1418, or the like. The memory 1422 is further configured to store HS signals, S1 COMs, S2 COMs, S3 COMs, S4 COMs, EMATs, SIs, DIs, and the like The sensing circuit 1424 is configured to monitor intrinsic electrical CA signals within the heart. The sensing circuit 1424 is communicatively coupled to one or more sensing electrodes 1412, 1426 located on or extending from the housing 102. The sensing electrodes 1426 is shown located along one or more sides of the shell 1408 but may additionally or alternatively be located along the second end 1406 of the housing 1402. The sensing electrode 1426 senses electrical activity, such as physiologic and pathologic behavior and events, and provide sensed signals to the sensing circuit 1424 in response. In an alternative embodiment, the pulsing electrode 1412 doubles as a sensing electrode, such that the pulsing electrode 1412 is used to deliver stimulation pulses and, in-between pulses, monitors the electrical activity within the tissue of interest for the sensing circuit 1424.

Optionally, the IMD 1400 may include a heart rate (HR) sensor 1427 configured to obtain HR data indicative of a patient heart rate. For example, the HR sensor 1427 may sense a blood temperature indicative of a core body temperature of the patient. The processor 1420 is further configured to produce a relative temperature signal based on the blood temperature signal. The processor 1420 further produces a moving baseline temperature signal based on the relative temperature signal, produces a proportional response signal based on the relative temperature signal and the moving baseline temperature signal, and produces a sensor indicated rate response signal based on the proportional response signal and a base rate. The sensor indicated rate response signal can also be based on a dip response signal and/or a slope response signal. When in a therapy mode, the processor 1420 is configured to adjust the at least one of the TR delay or SR BI based on the HR data. For example, the processor 1420 may be configured to adjust one or more pacing parameters to control a pacing rate based on the sensor indicated rate response signal. For example, the processor 1420 may adjust the AV delay, VV delay, PVARP blanking period and the like, based on the sensor indicated rate response signal.

Figure 16:
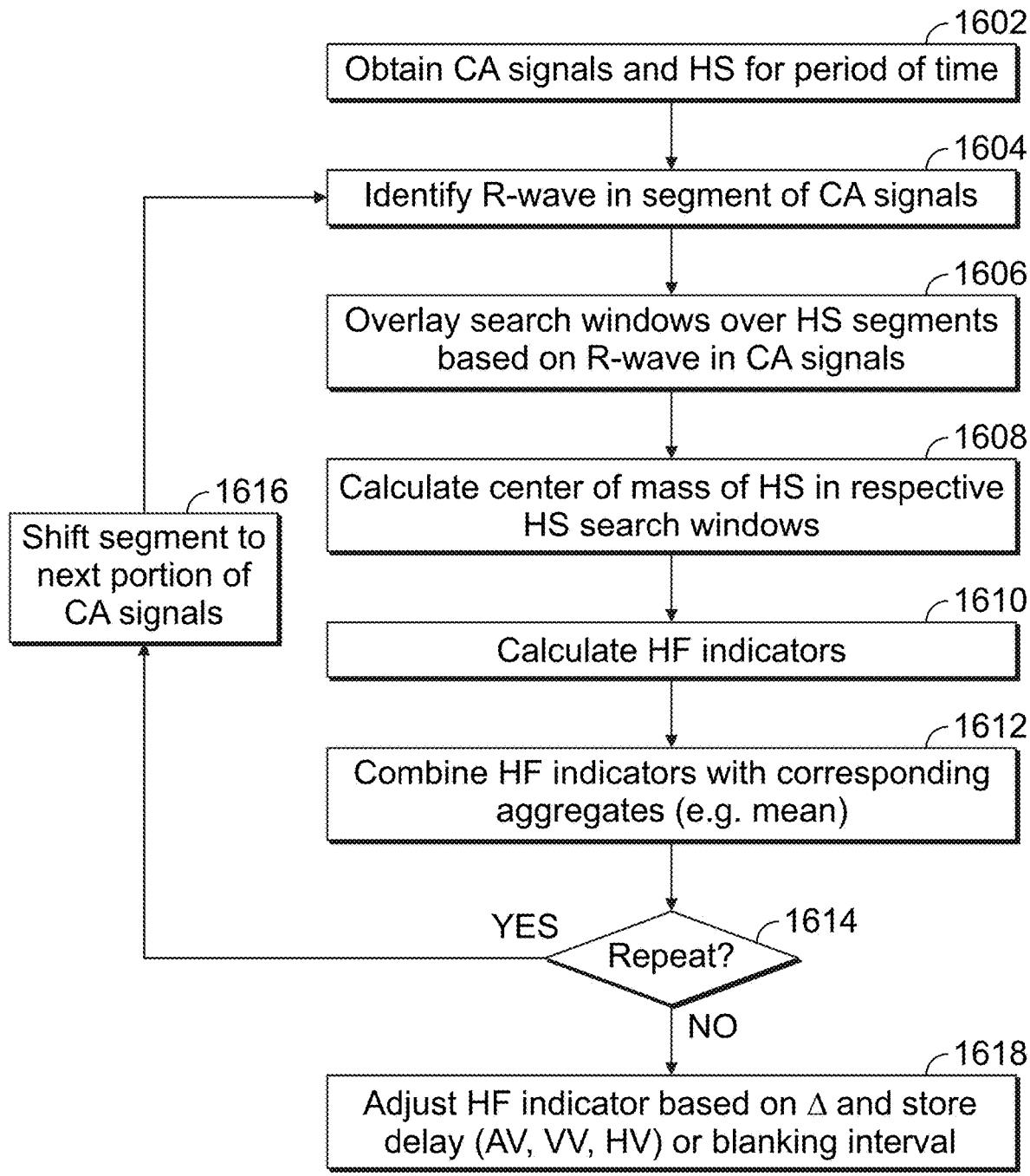
FIG. 16 illustrates a method for monitoring heart function based on heart sounds to define one or more therapy related delays and/or one or more sensing related BIs in accordance with embodiments herein.

FIG. 16 illustrates a method for monitoring heart function based on heart sounds to define one or more therapy related delays and/or one or more sensing related BIs in accordance with embodiments herein. The operations of FIG. 16 may be implemented when the IMD is in a calibration mode and may be implemented by hardware, firmware, circuitry and/or one or more processors housed partially an/or entirely within an IMD, a local external device, remote server or more generally within a healthcare system. Optionally, the operations of FIG. 16 may be partially implemented by an IMD and partially implemented by a local external device, remote server or more generally within a healthcare system. For example, the IMD includes IMD memory and one or more IMD processors, while each of the external devices/systems (ED) (e.g., local, remote or anywhere within the healthcare system) include ED memory and one or more ED processors.

At 1602, one or more processors obtain CA signals and HS signals for a common period of time. For example, the period of time may represent a predetermined number of seconds, minutes or otherwise, or alternatively a number of cardiac beats. The CA signals may be sensed utilizing one or more combinations of electrodes and sensing circuitry within coupled to the IMD. The HS signals may be sensed utilizing the monitoring sensor/system 1425 (e.g., a three-dimensional accelerometer and HS filtering circuitry) within the IMD.

At 1604, the one or more processors identify a COI within a segment of the CA signals. For example, the segment may have a duration approximating the duration of a single heartbeat and the COI may represent the peak of the Q-wave, peak of the R-wave or otherwise.

At 1606, the one or more processors overlay HS search windows onto respective HS segments of the HS signals where the positions of the HS search windows are determined based on the COI from the CA signal segment. For example, the HS search windows may correspond to the S1 and S2 heart sounds. Additionally or alternatively, the Hs search windows may correspond to S3 and S4 heart sounds, and/or any combination of S1, S2, S3 and S4 heart sounds. When the COI represents the peak of the R-wave, an S1 search window may be positioned to begin at the same time as the R-wave peak or a predetermined first interval before or after the R-wave peak. The S2 search window may then be positioned to begin a predetermined second interval after the R-wave peak and/or a predetermined third interval after the end of the S1 search window. The S3 and/or S4 search windows may be positioned to begin corresponding predetermined intervals after the R-wave peak and/or corresponding predetermined intervals after the end of the S1 and/or S2 search windows. The S1, S2, S3 and S4 search windows each have a corresponding duration that is sufficient to span from prior to a beginning and extend past an ending of the corresponding S1, S2, S3 and S4 heart sounds of interest. For example, the S1, S2, S3 and S4 search windows may be preprogrammed to be 250 ms each or to have different durations.

At 1608, the one or more processors calculate a center of mass for at least one heart sound of interest to obtain a corresponding at least one HS COM. For example, HS COMs may be calculated for the S1 and S2 heart sounds to obtain an S1 COM and an S2 COM. Additionally or alternatively, COMs may be calculated for the S3 and S4 heart sounds, to obtain an S3 COM and an S4 COM. As explained above, the COM represents a center of mass for the corresponding HS signals within the corresponding search window. The calculation of the COMs may utilize Equation 1 discussed above, but for the corresponding search window. In the above example, the search window has a length corresponding to 250 data points. Optionally, search windows for different types of HS may have different lengths (e.g., the S1 search window includes 250 data points, while the S3 search window includes 300 data points). The resulting S1 COM, S2 COM, S3 COM and/or S4 COM represent first, second, third and/or fourth points in time, respectively, along a timeline corresponding to the CA signals and HS signals.

At 1610, the one or more processors calculate one or more HF indicators. Examples of HF indicators include EMAT, SI, DI, S1-S1 interval, S2-S2 interval, S3-S3 interval, S4-S4 interval. S1-R-wave peak interval, S2-R-wave peak interval, S3-R-wave peak interval, S4-R-wave peak interval and the like. The DI is calculated as the difference between the S1_COM and the S2_COM. The S1-S1 interval is calculated as the time period between successive S1_COMs (e.g., S1_COM(t1)–S1_COM(t2), where t1 and t2 correspond to points in time of successive S1_COMs). The S2-S2 interval is calculated as the time period between successive S2_COMs. The S3-S3 interval is calculated as the time period between successive S3_COMs. The S4-S4 interval is calculated as the time period between successive S4_COMs. Additionally or alternatively, the HF indicator may be the interval between select combinations of heart sounds, such as the interval between S1 and S4 (S1-S4 interval), the interval between S2 and S4 (S2-S4 interval), the interval between S3 and S4 (S3-S4 interval), and the like. Additionally, or alternatively, the HF indicator may be an interval between a HS and a CA signal COI, where the CA signal COI is in the same/current cardiac cycle as the HS or the CA signal COI is in the next cardiac cycle following the HS. For example, the HF indicator may be an interval between S1, S2, S3 or S4 and the R-wave peak of the next successive cardiac cycle (e.g., S1-R-wave peak, S2-R-wave peak, S3-R-wave peak, S4-R-wave peak). As one example, the S4-to-R-wave peak interval may be calculated as the interval=S4_COM–R_wave_loc, where R_wave_loc represents a point in time at which the peak of the R-wave occurs.

At 1612, the one or more processors combine a most recently calculated HF indicator with an aggregate set of previously calculated HF indicators. For example, the one or more processors combine the most recently DI with an aggregate set of previously calculated DIs. Additionally or alternatively, the one or more processors combine the most recently S4-R-wave peak interval with an aggregate set of previously calculated S4-R-wave peak interval. Additionally or alternatively, the one or more processors combine the most recently calculated S4-S4 interval with an aggregate set of previously calculated S4-S4 intervals, and/or the most recently calculated S2-R-wave peak interval with an aggregate set of previously calculated S2-R-wave peak intervals.

It is recognized the multiple different types of HF indicators may be determined during a single iteration through the operations at 1604 to 1612. For example, one value may be calculated for all or a portion of the EMAT, SI, DI, S1-S1 interval, S2-S2 interval, S3-S3 interval, S4-S4 interval. S1-R-wave peak interval, S2-R-wave peak interval, S3-R-wave peak interval, S4-R-wave peak interval and the like.

At 1614, the one or more processors determine whether to repeat the operations at 1604-1612. The operations at 1604-1612 are repeated for the CA signals and HS signals obtained for a select period of time. For example, if the period to time corresponds to one minute, while each iteration through the operations at 1604-1612, the one or more processors analyze a one second segment, the operations at 1604-1612 will be repeated 60 or more times. Based on the decision at 1614, flow branches to 1616 or to 1618.

At 1616, the one or more processors shift the segment to be analyzed to a next portion of the HS and CA signals. For example, when the CA signal segment that is analyzed is one second in length, the segment may be shifted a full one second forward in time such that the next segment does not overlap the prior segment. Alternatively, the segment may be shifted a percentage of the length of the segment (e.g., 25%), such that the next segment partially overlaps the prior segment. Thereafter, the operations at 1604-1612 are repeated for the next segment of the CA signals. The next R-wave is detected, which then defines the positions for the next S1 and S2 search windows. New HS COMs are calculated for the heart sounds within the corresponding HS search windows. New HF indicators are calculated based on the HS COMs (and optionally on the CA signal COI). The new values are then mathematically combined with the aggregates, such as maintaining an average or mean over the results from each iteration through 1604-1612.

Optionally, the operation at 1612-1616 may be omitted entirely when it is desirable to use a single beat to calculate an individual HF indicator. At 1614, when the process determines that the entire CA signals and HS signals have been analyzed, flow moves to 1618.

At 1618, the one or more processors calculate one or more TR delay and/or one or more SI BI based on the corresponding HF indicators and one or more corresponding delta values. As explained herein, the one or more processors is further configured to manage delivering of therapy based on at least one of the TR delay or SR BI. For example, the one or more TR delays may correspond to the AV delay, the VV delay, the AH delay, the HV delay and the like. The AV delay represents a delay, following an intrinsic or paced atrial event, before the IMD will pace the ventricle if no intrinsic ventricular event occurs. The VV delay represents a delay, following an intrinsic or paced LV or RV event, before the IMD will pace the opposite ventricle if no intrinsic ventricular event occurs (e.g., intrinsic LV event followed by paced RV event, or vice versa). The AH delay represents a delay, following an intrinsic or paced atrial event, before the IMD will pace the HIS bundle if no intrinsic HIS event occurs. The HV delay represents a delay, following an intrinsic or paced HIS bundle event, before the IMD will pace the ventricle if no intrinsic ventricular event occurs.

Figure 17:
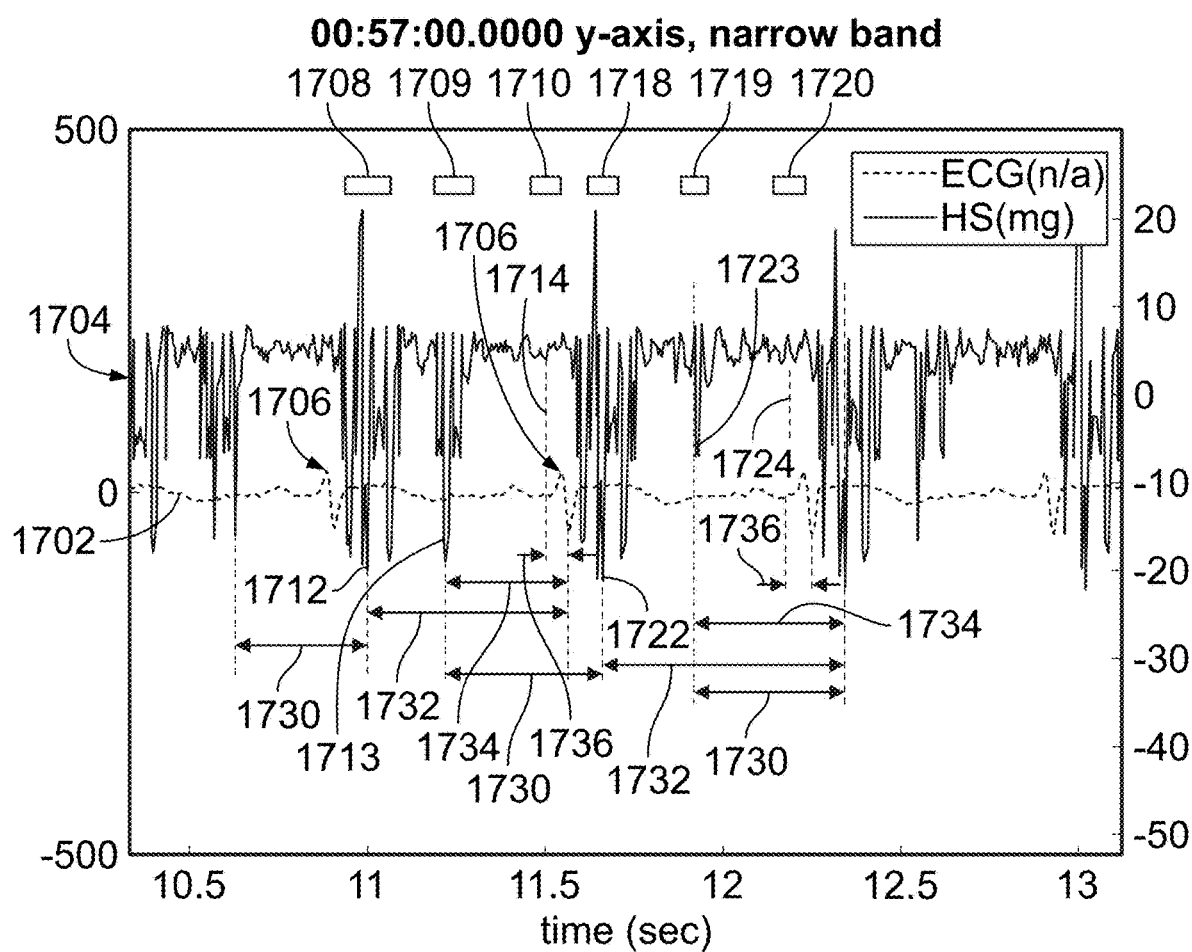
FIG. 17 illustrates a graphical example of the analysis is applied during the operations of FIG. 16.

In FIG. 17 illustrates a graphical example of the analysis is applied during the operations of FIG. 16. The process collects the CA signals 1702 and the HS signals 1704 over a period of time, such as 3 seconds. During the period of time, the patient experiences 4 heartbeats. In connection with each heart beat, a COI 1706 is identified and utilized to overlay one or more HS search windows onto respective HS segments of the HS signals 1704. For example, S1, S2 and S4 search windows 1708, 1709, 1710 may be overlaid. If the process calculates a COM in connection with the HS search window, such as S1 COM 1712, S2 COM 1713 and S4 COM 1714. FIG. 17 also illustrates S1, S2 and S4 search windows 1718, 1719, and 1720 for the subsequent heart beat, in connection with the process determines in S1 COM 1722, S2 COM 1723, and S4 COM 1724.

At 1610, the process calculates one or more HF indicators for a series of heartbeats. For example, the HF indicator may include one or more of the DI 1730, S1-R-wave peak interval is 1732, S2-R-wave peak interval 1734, and/or S4-R-wave peak interval 1736. The HF indicators DI 1730, S1-R-wave peak interval 1732, S2-R-wave peak interval 1734, and/or S4-R-wave peak interval 1736 are shown in connection with 2 subsequent heartbeats.

The process repeats and combines individual HF indicators with the corresponding aggregate HF indicator. For example, the DI values across a series of beats are combined to form an average DI value, a mean DI value and the like. Additionally or alternatively, the individual S1-R-wave peak intervals are combined to form an aggregate S1-R-wave peak interval. Additionally or alternatively, the individual S2-R-wave peak intervals are combined to form an aggregate S2-R-wave peak interval. Additionally or alternatively, the individual S4-R-wave peak intervals are combined to form an aggregate S4-R-wave peak interval. When the operations at 1604-1614 are completed, flow moves to 1618, where one or more of the aggregate HF indicators are adjusted to form/calculate a corresponding TR delay and/or SR BI.

By way of example, at 1618, the one or more processors calculate, as a TR delay, the AV delay (or other TR delay) by subtracting a delta A value from aggregate the DI. When the diastolic interval (e.g., S2_COM–S1_COM) is utilized, a clinician may program the A value to be Xms. The one or more processors calculates an AV delay by subtracting the Δ value from the aggregate DI.

Additionally or alternatively, the one or more processors may calculate, as a TR delay, the S4-R-wave peak interval (as noted at 1736 in FIG. 17). The S4-R-wave peak interval may be utilized as a S4-R delay, for which a timer is initiated upon detection of the S4 heart sound. A paced event may be delivered to the RV upon expiration of the S4-4 delay, in the event that an intrinsic ventricular event is not detected before the S4-R delay expires. Additionally or alternatively, the one or more processors may calculate, as a TR delay, the S1-R-wave peak interval (as noted at 1732 in FIG. 17). The S1-R-wave peak interval may be utilized as a S1-R delay, for which a timer is initiated upon detection of the S1 heart sound. Additionally or alternatively, the one or more processors may calculate, as a TR delay, the S2-R-wave peak interval (as noted at 1734 in FIG. 17). The S2-R-wave peak interval may be utilized as a S2-R delay, for which a timer is initiated upon detection of the S2 heart sound. The foregoing examples related to an implementation in which a leadless IMD is implanted in the RV. Additionally or alternatively, the foregoing, implementations may be applied to a leadless IMD that is implanted in or proximate to the LV. In the case of an LV Implantation, the delta values may be adjusted by the clinician to account for timing between intrinsic or paced atrial events and LV pacing.

Figure 18:
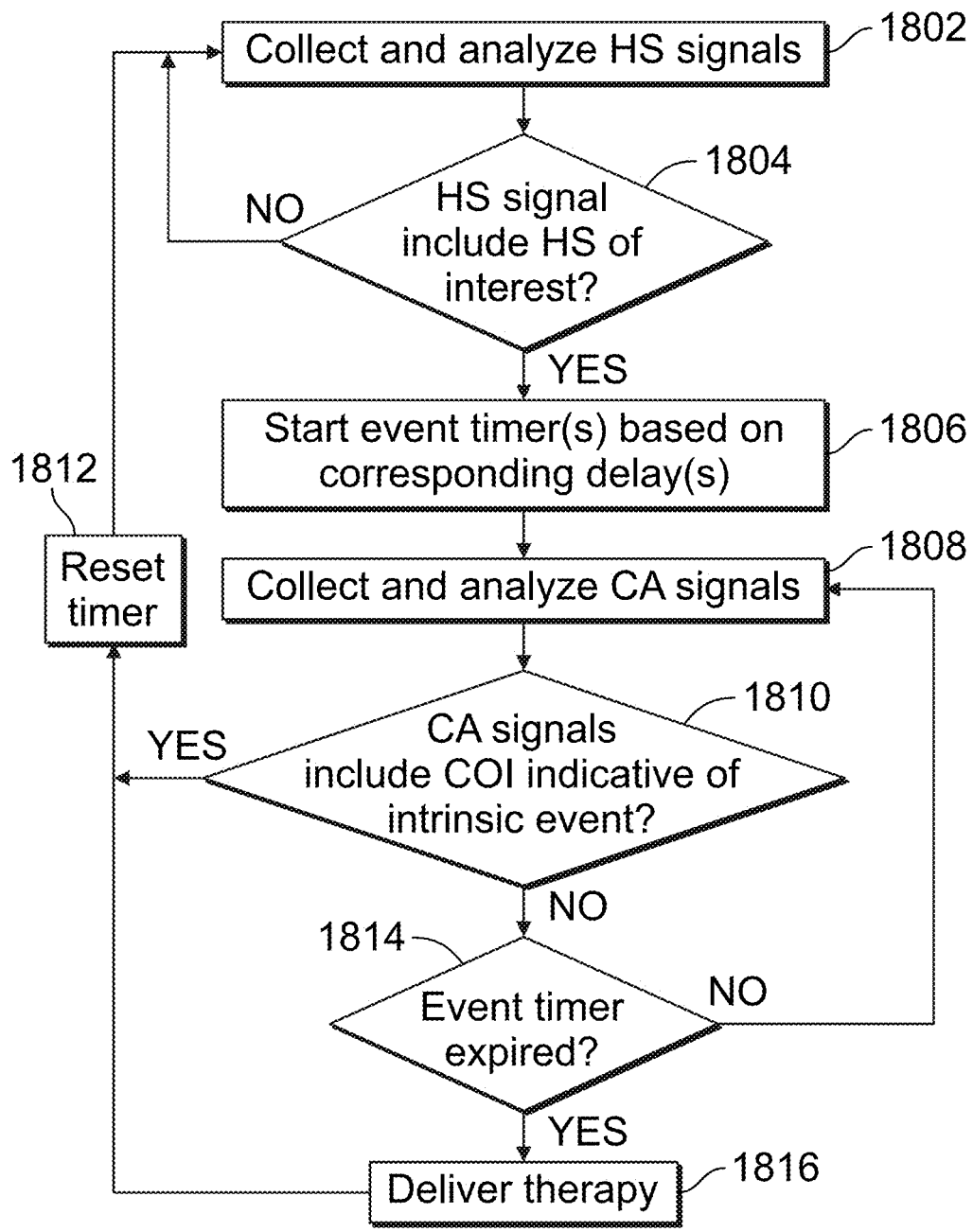
FIG. 18 illustrates a process implemented by a leadless IMD to manage therapy, and/or sensing based on the HF indicators acquired in accordance with embodiments herein.

FIG. 18 illustrates a process implemented by a leadless IMD to manage therapy, and/or sensing based on the HF indicators acquired in accordance with embodiments herein. The operations of FIG. 18 may be implemented when the IMD is in a therapy mode and on a beat by beat basis.

At 1802, the one or more processors of the leadless IMD manage circuitry and other electronic components within the IMD to collect and analyze HS signals in connection with a current heartbeat. The one or more processors analyze the HS signals to identify one or more heart sounds of interest, such as the S1, S2, S3, and/or S4. The identification of the HS of interest may include overlaying a HS search window over a segment of the HS signals.

The alignment of the HS search window may be based on timing derived from prior HS COMs and/or prior COI within the DCA signals. For example, a current S1 search window may be positioned at a predetermined number of milliseconds to begin after a peak of the R-wave in the previous heartbeat. Additionally or alternatively, a current S2, S3, and/or S4 search window may be positioned at a predetermined number of milliseconds to begin after a peak of the R-wave in the previous heartbeat. As another example, the HS search windows may be based on a timing of prior COM for the same heart sound. For example, over a series of beats, it may be determined that the average interval between successive S1 COM is X milliseconds. Accordingly, a current S1 search window may be timed to begin X milliseconds after a beginning of the preceding S1 search window. Similarly, a current S2, S3, and/or S4 search window may be timed to begin why milliseconds after a beginning of the corresponding one of the preceding S2, S3, and/or S4 search window. As another example, the S2, S3, and/or S4 search windows may be timed to begin a programmed or IMD determined number of milliseconds after the beginning or end of the current S1 search window. The analysis at 1802 may simply identify a peak of a heart sound of interest, or a more complex process that identifies a COM for the heart sound of interest.

At 1804, the one or more processors determine whether a current segment of the HS signals include an HS of interest, such as an S1 heart sound, S2 heart sound, S3 heart sound, and/or S4 heart sound. When the current segment of the HS signals does not include the heart sound of interest, flow returns to 1802. The process repeats until the heart sound of interest is identified (e.g., S1 peak, S1 COM, S2 peak, S2 COM, S3, peak, S3 COM, S4, peak, S4, COM).

When the heart sound of interest is identified at 1804, flow moves to 1806. At 1806, the one or more processors of the IMD started/initiated one or more event timers. The event timers may correspond to a TR delay and/or an SR BI. For example, the event timer may correspond to an AV delay timer that is started upon detection of a heart sound of interest. For example, when the S2 heart sound is identified at 1804, the AV delay timer may be started. As discussed above in connection with FIG. 16, the AV delay is set to correspond to the DI minus a delta value programmed by the clinician. By subtracting the delta value from the DI, embodiments herein are able to estimate the time at which should be paced following occurrence of the S2 heart sound and a current heartbeat.

The AV delay represents one type of delay, utilized to manage ventricular pacing. Other TR related delays may similarly be utilized to manage ventricular pacing. For example, the event timer may correspond to a S4-R delay. The S4-R delay that is started upon detection of an S4 heart sound of interest. When the S4 heart sound is identified at 1804, the S4-4 delay timer may be started. As discussed above in connection with FIG. 16, the S4-R HF delay is set to correspond to an aggregate S4-R HF indicator calculated aqt 1612 over multiple prior beats. The aggregate S4-RV HF indicator may be utilized as the S4-R delay alone or in combination with the addition/subtraction of a programmed delta value.

At 1808, the one or more processors of the IMD manage the device to collect and analyze DCA signals. At 1810, the one or more processors determine whether the CA signals include a COI indicative of an intrinsic event. For example, the one or more processors may determine whether the CA signals include an R-wave indicative of an intrinsic ventricular contraction.

When a COI (e.g, intrinsic ventricular contraction) is identified at 1810, the process determines that no therapy is needed, and flow moves to 1812. At 1812, the one or more processors reset the event timer(s). When no COI. Indicative of an intrinsic event is identified at 1810, flow moves to 1814. At 1814, the process determines whether the event timer has expired. If the event timer has not expired, flow returns to 1808 where additional CI signals are collected and analyzed. When the event timer does expire at 1814, flow continues to 1816. At 1816, the leadless IMD delivers a corresponding therapy. In the present example, the leadless IMD is implanted in the RV and, accordingly, RV pacing therapy is delivered. For example, the IMD delivers a ventricular therapy when an intrinsic ventricular event is not detected before the AV timer times out. Thereafter, flow moves to 1812, where the various event timers are reset. Flow then returns to 1802, where the leadless IMD begins to collect new heart sound signals in search of the next heart sound of interest.

The foregoing process is described in connection with a leadless IMD implanted in or proximate to the RV or LV. When implanted in or proximate to a ventricle, the IMD may utilize at least one TR delay that includes at least one of an HS-HS interval or an HS-R-wave interval calculated by combining a delta value with a corresponding at least one of the HS-HS interval or the HS-R-wave interval. In the present example, the one or more processors are configured to: identify an HS of interest; in response to the identifying the HS of interest, start a timer corresponding to the at least one of the HS-HS interval or HS-R-wave interval; and deliver a ventricular therapy when an intrinsic ventricular event is not detected before the timer times out.

Additionally or alternatively, the process may be applied in connection with a leadless IMD implanted in or proximate to the HIS bundle, RA, LA and elsewhere. When implanted at the HIS bundle, the event timer may correspond to a H-V delay that is defined by combining (e.g., subtracting/adding) a delta value and the SI, DI, a HS-HS interval (e.g., one or more of the S1-S1 interval, S2-S2 interval, S3-S3 interval, and/or S4-S4 interval), and HS-R-wave interval (e.g., one or more of an S1-R-wave interval, S2-R-wave interval, S3-R-wave interval, and/or S4-R-wave interval) and the like. In general, the "HS-HS interval" is used to refer to one or more of the S1-S1 interval, S2-S2 interval, S3-S3 interval, and/or S4-S4 interval. In general, the "HS-R-wave interval" is used to refer to one or more of the S1-R-wave interval, S2-R-wave interval, S3-R-wave interval, and/or S4-R-wave. The R-wave COI may be the R-wave peak, R-wave COM, R-wave start/end and the like.

When implanted in or proximate to the RA or LA, the event timer may correspond to an VA delay that is defined by subtracting/adding a delta value to the SI, DI, S1-S1 interval, S2-S2 interval, S3-S3 interval, S4-S4 interval. S1-R-wave interval, S2-R-wave interval, S3-R-wave interval, S4-R-wave interval and the like, where the HS of interest is indicative of ventricular activity and the IMD is configured to deliver an RA or LA paced event if a VA timer times out before detecting an intrinsic atrial event.

Figure 19:
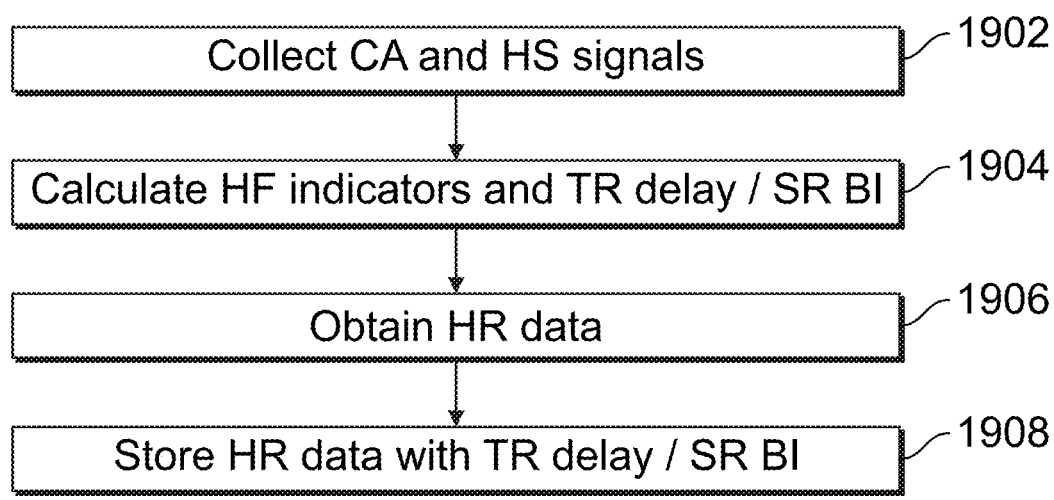
FIG. 19 illustrates an alternative embodiment in which the leadless IMD determines TR delays and/or SR BIs in connection with a rate adaptive mode such as to account for patient activity.

FIG. 19 illustrates an alternative embodiment in which the leadless IMD determines TR delays and/or SR BIs in connection with a rate adaptive mode such as to account for patient activity. At 1902, one or more processors obtain CA signals and HS signals for a common period of time. For example, the period of time may represent a predetermined number of seconds, minutes or otherwise, or alternatively a number of cardiac beats. At 1904, the one or more processors calculate one or more HF indicators, such as by utilizing the processes described herein. At 1904, the one or more processors also calculate one or more TR delay and/or one or more SI BI based on the corresponding HF indicators and one or more corresponding delta values, such as by utilizing the processes described herein.

At 1906, the one or more processors obtain heart rate (HR) data. The HR data may be obtained from a rate adaptive signal that is generated by a motion sensor (e.g., accelerometer), a temperature sensor and the like. When utilizing a temperature sensor, the IMD may implement, in combination with the HS based operations herein, the rate adaptive processes described in U.S. patent application Ser. No. 17/393,634, filed Aug. 4, 2021 and titled "SYSTEM AND METHOD FOR RATE MODULATED CARDIAC THERAPY UTILIZING A TEMPERATURE SENSOR", the complete subject matter of which is expressly incorporated herein by reference in its entirety. For example, as noted above, the IMD may include a temperature sensor configured to sense a blood temperature signal indicative of a core body temperature of the patient. The one or more processors is further configured to produce a relative temperature signal based on the blood temperature signal. The one or more processors further produce a moving baseline temperature signal based on the relative temperature signal, produce a proportional response signal based on the relative temperature signal and the moving baseline temperature signal, and produce a sensor indicated rate response signal based on the proportional response signal and a base rate. The sensor indicated rate response signal can also be based on a dip response signal and/or a slope response signal. Additionally, a pacing rate is controlled based on the sensor indicated rate response signal.

At 1908, the one or more processors store the HR data with the TR delay(s) and/or with the SR BI(s). The one or more processors is configured to store the HR data with the at least one of TR delay or the SR BI, such as to associate a first HR with at least one of a first TR delay or first SR BI and to associate a second HR with at least one of a second TR delay or second SR BI. For example, a first AV delay, first HV delay, first PVARP BI and the like, are stored with a heart rate of 60 bpm, while a second AV delay, second HV delay, second PVARP BI and the like, are stored with a heart rate of 90 bpm. Additionally or alternatively, heart rate ranges may be defined, such as below 50 bpm, 50-70 bpm, 70-90 bpm, etc. where each HR range is assigned a separate AV delay, PVARP blanking interval and the like.

The process of FIG. 19 may be repeated periodically and/or during a calibration process under direction of a clinician, in connection with communication with a smart phone or home monitoring device, independently at a choice by the patient and the like.

The process of FIG. 18 may be implemented in connection with a rate adaptive IMD. To do so, while collecting and analyzing HS signals (at 1802) or thereafter, the one or more processors of the IMD obtain HR data. For example, the HR data may be obtained from a rate adaptive signal that is generated by a motion sensor (e.g., accelerometer), a temperature sensor and the like. The one or more processors utilize the HR data to identify one or more corresponding TR delay(s) and/or SR BI(s) that were previously stored and associated with a current HR. When in a therapy mode, the one or more processors are configured to adjust the at least one of the TR delay or SR BI based on the HR data. For example, at 1806, the one or more processors may determine that the patients HR is between 50 bpm and 70 bpm and therefore the AV delay, HV delay, PVARP BI and the like, associated with the HR range of 50-70 bpm, should be utilized.

Embodiments may be implemented in connection with one or more IMDs. Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. The IMD may measure electrical and/or mechanical information. For example, the IMD may include one or more structural and/or functional aspects of the device(s) described in U.S. Pat. No. 9,333,351, entitled "NEUROSTIMULATION METHOD AND SYSTEM TO TREAT APNEA" issued May 10, 2016 and U.S. Pat. No. 9,044,610, entitled "SYSTEM AND METHODS FOR PROVIDING A DISTRIBUTED VIRTUAL STIMULATION CATHODE FOR USE WITH AN IMPLANTABLE NEUROSTIMULATION SYSTEM" issued Jun. 2, 2015, which are hereby incorporated by reference. The IMD may monitor transthoracic impedance, such as implemented by the CorVue algorithm offered by St. Jude Medical. Additionally or alternatively, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015 and U.S. Pat. No. 8,831,747, entitled "LEADLESS NEUROSTIMULATION DEVICE AND METHOD INCLUDING THE SAME" issued Sep. 9, 2014, which are hereby incorporated by reference. Additionally or alternatively, the IMD may include one or more structural and/or functional aspects of the device(s) described in U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016, which are hereby incorporated by reference. Additionally or alternatively, the IMD may be a subcutaneous IMD that includes one or more structural and/or functional aspects of the device(s) described in U.S. application Ser. No. 15/973,195, entitled "SUBCUTANEOUS IMPLANTATION MEDICAL DEVICE WITH MULTIPLE PARASTERNAL-ANTERIOR ELECTRODES" filed May 7, 2018; U.S. application Ser. No. 15/973,219, entitled "IMPLANTABLE MEDICAL SYSTEMS AND METHODS INCLUDING PULSE GENERATORS AND LEADS" filed May 7, 2018; U.S. application Ser. No. 15/973,249, entitled "SINGLE SITE IMPLANTATION METHODS FOR MEDICAL DEVICES HAVING MULTIPLE LEADS", filed May 7, 2018, which are hereby incorporated by reference in their entireties. Further, one or more combinations of IMDs may be utilized from the above incorporated patents and applications in accordance with embodiments herein. Embodiments may be implemented in connection with one or more subcutaneous implantable medical devices (S-IMDs). For example, the S-IMD may include one or more structural and/or functional aspects of the device(s) described in U.S. application Ser. No. 15/973,219, entitled "IMPLANTABLE MEDICAL SYSTEMS AND METHODS INCLUDING PULSE GENERATORS AND LEADS", filed May 7, 2018; U.S. application Ser. No. 15/973,195, entitled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The IMD may represent a passive device that utilizes an external power source and/or an active device that includes an internal power source. The IMD may deliver some type of therapy/treatment, provide mechanical circulatory support and/or merely monitor one or more physiologic characteristics of interest (e.g., PAP, CA signals, impedance, heart sounds). Additionally or alternatively, embodiments may be implemented in connection with one or more passive IMDS (PIMDs). Non-limiting examples of PIMDs may include passive wireless sensors used by themselves, or incorporated into or used in conjunction with other IMDs, such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, embodiments may implement one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties.

Additionally or alternatively, embodiments herein may be implemented in connection with the methods and systems described in "METHOD AND DEVICE FOR DETECTING RESPIRATION ANOMALY FROM LOW FREQUENCY COMPONENT OF ELECTRICAL CARDIAC ACTIVITY SIGNALS", U.S. application Ser. No. 16/869,733, filed on the same day as the present application, which is incorporated by reference herein in its entirety.

Additionally or alternatively, embodiments herein may be implemented in connection with the methods and systems described in "SYSTEM FOR VERIFYING A PATHOLOGIC EPISODE USING AN ACCELEROMETER", Provisional application Ser. No. 17/192,961, filed Mar. 5, 2021, which is incorporated by reference herein in its entirety.

All references, including publications, patent applications and patents, cited herein are hereby incorporated by reference to the same extent as if each reference were individually and specifically indicated to be incorporated by reference and were set forth in its entirety herein.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices, and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system for monitoring heart function based on heart sounds (HS), comprising:
    electrodes configured to sense electrical cardiac activity (CA) signals over a period of time;
    an HS sensor configured to sense HS signals over the period of time;
    memory to store specific executable instructions;
    one or more processors that, when executing the specific executable instructions, is configured to:
    identify a characteristic of interest (COI) of a heartbeat from the CA signals;
    overlay a HS search window onto an HS segment of the HS signals based on the COI from the CA signals;
    calculate a center of mass (COM) for at least one of S1 or S2 HS based on the HS segment of the HS signals within the search window to obtain a corresponding at least one of S1 COM or S2 COM;
    calculate at least one of an electromechanical activation time (EMAT) or a systolic interval (SI) based on the at least one of S1 COM or S2 COM; and
    record the at least one of the EMAT or SI.

2. The system of claim 1, wherein the HS search window includes S1 and S2 search windows, the one or more processors configured to overlay the S1 and S2 search windows over the corresponding HS segments.

3. The system of claim 2, wherein the one or more processors are configured to align the S1 search window over the corresponding HS segment to begin at or near an R-wave peak, the R-wave peak representing the COI.

4. The system of claim 2, wherein the one or more processors are configured to align the S2 search window over the corresponding HS segment to begin a predetermined interval after one of an end of the S1 search window or an R-wave peak, the R-wave peak representing the COI.

5. The system of claim 1, wherein the S1 COM and S2 COM represent corresponding points in time along the CA and HS signals.

6. The system of claim 1, wherein the COI occurs at a COI point in time along the CA signals, the one or more processors configured to calculate the EMAT by subtracting the S1 COM from the COI point in time.

7. The system of claim 1, wherein the one or more processors are configured to calculate the SI as a difference between the S1 COM and the S2 COM.

8. The system of claim 1, further comprising an implantable medical device (IMD), the memory and the one or more processors including an IMD memory and an IMD processor, respectively, the IMD processor configured to perform at least one of the identify, overlay or calculate operations.

9. The system of claim 8, further comprising an external device (ED) configured to wireless communicate with the IMD, the memory and the one or more processors including an ED memory and an ED processor, respectively, the ED processor configured to perform at least one of the identify, overlay and calculate operations.

10. The system of claim 9, wherein the ED wirelessly receives the CA and HS signals, the ED processor is configured to perform the identify, overlay and calculate operations.

11. The system of claim 1, wherein the HS sensor includes an accelerometer configured to collect multi-dimensional (MD) accelerometer data along at least two axes, the HS signals corresponding to the accelerometer data.

12. A computer implemented method for monitoring heart function based on heart sounds (HS), the method comprising:
    obtaining electrical cardiac activity (CA) signals, sensed at implantable electrodes, over a period of time;
    obtaining HS signals, sensed by an implantable HS sensor, over the period of time;
    under control of one or more processors,
    identifying a characteristic of interest (COI) of a heartbeat from the CA signals;
    overlaying a HS search window onto an HS segment of the HS signals based on the COI from the CA signals;
    calculating a center of mass (COM) for at least one of S1 or S2 HS based on the HS segment of the HS signals within the search window to obtain a corresponding at least one of S1 COM or S2 COM;
    calculating at least one of an electromechanical activation time (EMAT) or a systolic interval (SI) based on the at least one of S1 COM or S2 COM; and
    recording the at least one of the EMAT or SI.

13. The method of claim 12, wherein the HS search window includes S1 and S2 search windows, the one or more processors configured to overlay the S1 and S2 search windows over corresponding HS segments.

14. The method of claim 13, wherein the aligning operation includes aligning the S1 search window over the HS signals to begin at or near an R-wave peak, the R-wave peak representing the COI.

15. The method of claim 13, wherein the aligning operation further comprises aligning the S2 search window over the HS signals to begin a predetermined interval after one of an end of the S1 search window or an R-wave peak, the R-wave peak representing the COI.

16. The method of claim 12, wherein the COI occurs at a COI point in time along the CA signals, the method calculating the EMAT by subtracting the S1 COM from the COI point in time.

17. The method of claim 12, further comprising storing the EMAT and SI over a period of time and monitoring an EMAT trend and an SI trend over a period of time for an indication of a change in a physiologic or non-physiologic condition.

18. The method of claim 12, further comprising wirelessly transmitting the CA and HS signals from an implantable medical device (IMD) to an external device (ED), the ED performing at least one of the identifying, overlaying, calculating and recording operations.

19. The method of claim 12, wherein the identify, overlay or calculate operations are implemented by an implantable medical device.

20. A computer implemented method for monitoring heart function based on heart sounds (HS), the method comprising:
   obtaining electrical cardiac activity (CA) signals, sensed at implantable electrodes, over a period of time;
   obtaining HS signals, sensed by an implantable HS sensor, over the period of time;
   under control of one or more processors,
   identifying a characteristic of interest (COI) of a heartbeat from the CA signals;
   overlaying a HS search window onto an HS segment of the HS signals based on the COI from the CA signals;
   calculating a center of mass (COM) for at least one of S1 or S2 HS based on the HS segment of the HS signals within the search window to obtain a corresponding at least one of S1 COM or S2 COM;
   calculating at least one of an electromechanical activation time (EMAT) or a systolic interval (SI) based on the at least one of S1 COM or S2 COM; and
   recording the at least one of the EMAT or SI;
   wherein the calculating the S1 COM comprises:
   calculating products of i) amplitudes of the HS signals at points along the S1 search window and ii) positions of the corresponding points along the S1 search window;
   summing the products to form a first sum;
   summing the amplitudes of the HS signals at the points to form a second sum; and
   dividing the first sum by the second sum.

* * * * *